United States Patent [19]
Hinuma et al.

[11] Patent Number: 6,048,711
[45] Date of Patent: Apr. 11, 2000

[54] HUMAN G-PROTEIN COUPLED RECEPTOR POLYNUCLEOTIDES

[75] Inventors: Shuji Hinuma; Shoji Fukusumi; Yuji Kawamata, all of Ibaraki, Japan

[73] Assignee: Takeda Chemical Industries, Ltd., Tsukuba Ibaraki, Japan

[21] Appl. No.: 08/959,381

[22] Filed: Oct. 28, 1997

[30] Foreign Application Priority Data

Oct. 29, 1996 [JP] Japan ..................................... 8-286823

[51] Int. Cl.⁷ .......................... C12N 15/09; C07K 14/705
[52] U.S. Cl. .................... 435/69.1; 536/23.5; 435/252.3; 435/254.11; 435/320.1; 435/325
[58] Field of Search .......................... 536/23.5; 435/69.1, 435/325, 252.3, 254.11, 320.1

[56] References Cited

PUBLICATIONS

Z. Zeng, et al., "A Novel Endothelin Receptor Type–B–like Gene Enriched in the Brain", Biochemical and Biophysical Research Communications, 233:559–567 (1997).

*Primary Examiner*—Sally Teng
*Attorney, Agent, or Firm*—William T. Han; Ratner & Prestia; William T. King

[57] ABSTRACT

A novel G-protein coupled receptor protein, a partial peptide and their salts are disclosed. DNA encoding the receptor protein, production of the receptor protein, determination of a ligand to the receptor protein, a method for screening for compounds which inhibit ligand binding to the receptor protein, a kit for screening for such compounds are also disclosed. The receptor protein, its partial peptide and their salts are used for screening for candidate compounds of drugs and the like.

14 Claims, 9 Drawing Sheets

```
  1 ATCCTAATACGACTCACTATAGGGCTCGAGCGGCCGCCCGGGCAGGTCTCTGGAGTCAGA   60
  1                                                                1

61 TCTGGGTTGTGGGCCTTGCTCTGCCTTGTATCAACTATGTGGCAAGTGACTGACCTCTAC  120
  1                                                                1

121 AAACCTCAGATTTGTGATCTGAGATTAATCAAGGGTTAATTGAGAAACCAGCTGAGTGCT  180
  1                                                                1

181 AGCACCTAGTAAGTGTTCAGTAAGTGACAGTGACGGTTATTGCTGAGTCTTGAATGGAGG  240
  1                                                                1

241 AGCTGCCTTAGAATCAGGAGACCTGCGCCCCAGTTCCCATTCTGCCCCACCTCCCTGTGT  300
  1                                                                1

301 CACCCTAGGCAGGCCACATTTCCTCCCTAGTTTCAGGGGCCTGAAGCAGATGCCCTCTTA  360
  1                                                                1

361 GGGCCCCACAGCCTGACATGCTGTAGGGCCTGAGAAGCGGCGTCGTGGAGGACGAGATGT  420
  1                                                                1

421 GTGAGGGCAGCAAAGAGTGCTATGTGTCCAGCAGAGGGCCCTGCCCGGCCTGTGGCCGGA  480
  1                                                                1

481 GGCTGGGAGGGAGGGCAGGCGAGTGATGCCAGACGCCTGACTGGAGGCGGATCCAGCCGG  540
  1                                                                1

541 CCAGCTGCCTCTCTGGAGCCCAGCTCTTGGGCCCCCTGTACTCACCTGCTCTTCCTGGGC  600
  1                                                                1

601 TGGCTGTCTCCTGCTCATCCAGCCATGCGGTGGCTGTGGCCCCTGGCTGTCTCTCTTGCT  660
  1                    MetArgTrpLeuTrpProLeuAlaValSerLeuAla         12

661 GTGATTTTGGCTGTGGGGCTAAGCAGGGTCTCTGGGGGTGCCCCCCTGCACCTGGGCAGG  720
 13 ValIleLeuAlaValGlyLeuSerArgValSerGlyGlyAlaProLeuHisLeuGlyArg   32
```

FIG. 1A

```
 721 CACAGAGCCGAGACCCAGGAGCAGCAGAGCCGATCCAAGAGGGGCACCGAGGATGAGGAG  780
  33 HisArgAlaGluThrGlnGluGlnGlnSerArgSerLysArgGlyThrGluAspGluGlu   52

781 GCCAAGGGCGTGCAGCAGTATGTGCCTGAGGAGTGGGCGGAGTACCCCCGGCCCATTCAC  840
  53 AlaLysGlyValGlnGlnTyrValProGluGluTrpAlaGluTyrProArgProIleHis   72

841 CCTGCTGGCCTGCAGCCAACCAAGCCCTTGGTGGCCACCAGCCCTAACCCCGACAAGGAT  900
  73 ProAlaGlyLeuGlnProThrLysProLeuValAlaThrSerProAsnProAspLysAsp   92

901 GGGGGCACCCCAGACAGTGGGCAGGAACTGAGGGGCAATCTGACAGGGGCACCAGGGCAG  960
  93 GlyGlyThrProAspSerGlyGlnGluLeuArgGlyAsnLeuThrGlyAlaProGlyGln  112

961 AGGCTACAGATCCAGAACCCCCTGTATCCGGTGACCGAGAGCTCCTACAGTGCCTATGCC 1020
 113 ArgLeuGlnIleGlnAsnProLeuTyrProValThrGluSerSerTyrSerAlaTyrAla  132

1021 ATCATGCTTCTGGCGCTGGTGGTGTTTGCGGTGGGCATTGTGGGCAACCTGTCGGTCATG 1080
 133 IleMetLeuLeuAlaLeuValValPheAlaValGlyIleValGlyAsnLeuSerValMet  152

1081 TGCATCGTGTGGCACAGCTACTACCTGAAGAGCGCCTGGAACTCCATCCTTGCCAGCCTG 1140
 153 CysIleValTrpHisSerTyrTyrLeuLysSerAlaTrpAsnSerIleLeuAlaSerLeu  172

1141 GCCCTCTGGGATTTTCTGGTCCTCTTTTTCTGCCTCCCTATTGTCATCTTCAACGAGATC 1200
 173 AlaLeuTrpAspPheLeuValLeuPhePheCysLeuProIleValIlePheAsnGluIle  192

1201 ACCAAGCAGAGGCTACTGGGTGACGTTTCTTGTCGTGCCGTGCCCTTCATGGAGGTCTCC 1260
 193 ThrLysGlnArgLeuLeuGlyAspValSerCysArgAlaValProPheMetGluValSer  212

1261 TCTCTGGGAGTCACGACTTTCAGCCTCTGTGCCCTGGGCATTGACCGCTTCCACGTGGCC 1320
 213 SerLeuGlyValThrThrPheSerLeuCysAlaLeuGlyIleAspArgPheHisValAla  232

1321 ACCAGCACCCTGCCCAAGGTGAGGCCCATCGAGCGGTGCCAATCCATCCTGGCCAAGTTG 1380
 233 ThrSerThrLeuProLysValArgProIleGluArgCysGlnSerIleLeuAlaLysLeu  252

1381 GCTGTCATCTGGGTGGGCTCCATGACGCTGGCTGTGCCTGAGCTCCTGCTGTGGCAGCTG 1440
 253 AlaValIleTrpValGlySerMetThrLeuAlaValProGluLeuLeuLeuTrpGlnLeu  272
```

FIG. 1B

```
1441 GCACAGGAGCCTGCCCCCACCATGGGCACCCTGGACTCATGCATCATGAAACCCTCAGCC 1500
 273 AlaGlnGluProAlaProThrMetGlyThrLeuAspSerCysIleMetLysProSerAla  292

1501 AGCCTGCCCGAGTCCCTGTATTCACTGGTGATGACCTACCAGAACGCCCGCATGTGGTGG 1560
 293 SerLeuProGluSerLeuTyrSerLeuValMetThrTyrGlnAsnAlaArgMetTrpTrp  312

1561 TACTTTGGCTGCTACTTCTGCCTGCCCATCCTCTTCACAGTCACCTGCCAGCTGGTGACA 1620
 313 TyrPheGlyCysTyrPheCysLeuProIleLeuPheThrValThrCysGlnLeuValThr  332

1621 TGGCGGGTGCGAGGCCCTCCAGGGAGGAAGTCAGAGTGCAGGGCCAGCAAGCACGAGCAG 1680
 333 TrpArgValArgGlyProProGlyArgLysSerGluCysArgAlaSerLysHisGluGln  352

1681 TGTGAGAGCCAGCTCAACAGCACCGTGGTGGGCCTGACCGTGGTCTACGCCTTCTGCACC 1740
 353 CysGluSerGlnLeuAsnSerThrValValGlyLeuThrValValTyrAlaPheCysThr  372

1741 CTCCCAGAGAACGTCTGCAACATCGTGGTGGCCTACCTCTCCACCGAGCTGACCCGCCAG 1800
 373 LeuProGluAsnValCysAsnIleValValAlaTyrLeuSerThrGluLeuThrArgGln  392

1801 ACCCTGGACCTCCTGGGCCTCATCAACCAGTTCTCCACCTTCTTCAAGGGCGCCATCACC 1860
 393 ThrLeuAspLeuLeuGlyLeuIleAsnGlnPheSerThrPhePheLysGlyAlaIleThr  412

1861 CCAGTGCTGCTCCTTTGCATCTGCAGGCCGCTGGGCCAGGCCTTCCTGGACTGCTGCTGC 1920
 413 ProValLeuLeuLeuCysIleCysArgProLeuGlyGlnAlaPheLeuAspCysCysCys  432

1921 TGCTGCTGCTGTGAGGAGTGCGGCGGGGCTTCGGAGGCCTCTGCTGCCAATGGGTCGGAC 1980
 433 CysCysCysCysGluGluCysGlyGlyAlaSerGluAlaSerAlaAlaAsnGlySerAsp  452

1981 AACAAGCTCAAGACCGAGGTGTCCTCTTCCATCTACTTCCACAAGCCCAGGGAGTCACCC 2040
 453 AsnLysLeuLysThrGluValSerSerSerIleTyrPheHisLysProArgGluSerPro  472

2041 CCACTCCTGCCCCTGGGCACACCTTGCTGAGGCCCCAGTA                     2080
 473 ProLeuLeuProLeuGlyThrProCys***                                482
```

FIG. 1C

```
  1 ATCCTAATACGACTCACTATAGGGCTCGAGCGGCCGCCCGGGCAGGTCTCTGGAGTCAGA    60
  1                                                                1

61 TCTGGGTTGTGGGCCTTGCTCTGCCTTGTATCAACTATGTGGCAAGTGACTGACCTCTAC   120
  1                                                                1

121 AAACCTCAGATTTGTGATCTGAGATTAATCAAGGGTTAATTGAGAAACCAGCTGAGTGCT   180
  1                                                                1

181 AGCACCTAGTAAGTGTTCAGTAAGTGACAGTGACGGTTATTGCTGAGTCTTGAATGGAGG   240
  1                                                                1

241 AGCTGCCTTAGAATCAGGAGACCTGCGCCCCAGTTCCCATTCTGCCCCACCTCCCTGTGT   300
  1                                                                1

301 CACCCTAGGCAGGCCACATTTCCTCCCTAGTTTCAGGGGCCTGAAGCAGATGCCCTCTTA   360
  1                                                                1

361 GGGCCCCACAGCCTGACATGCTGTAGGGCCTGAGAAGCGGCGTCGTGGAGGACGAGATGT   420
  1                                                                1

421 GTGAGGGCAGCAAAGAGTGCTATGTGTCCAGCAGAGGGCCCTGCCCGGCCTGTGGCCGGA   480
  1                 MetCysProAlaGluGlyProAlaArgProValAlaGly         13

481 GGCTGGGAGGGAGGGCAGGCGAGTGATGCCAGACGCCTGACTGGAGGCGGATCCAGCCGG   540
 13 GlyTrpGluGlyGlyGlnAlaSerAspAlaArgArgLeuThrGlyGlyGlySerSerArg   33

541 CCAGCTGCCTCTCTGGAGCCCAGCTCTTGGGCCCCCTGTACTCACCTGCTCTTCCTGGGC   600
 33 ProAlaAlaSerLeuGluProSerSerTrpAlaProCysThrHisLeuLeuPheLeuGly   53

601 TGGCTGTCTCCTGCTCATCCAGCCATGCGGTGGCTGTGGCCCCTGGCTGTCTCTCTTGCT   660
 53 TrpLeuSerProAlaHisProAlaMetArgTrpLeuTrpProLeuAlaValSerLeuAla   73

661 GTGATTTTGGCTGTGGGGCTAAGCAGGGTCTCTGGGGGTGCCCCCCTGCACCTGGGCAGG   720
 73 ValIleLeuAlaValGlyLeuSerArgValSerGlyGlyAlaProLeuHisLeuGlyArg   93
```

FIG. 3A

```
 721 CACAGAGCCGAGACCCAGGAGCAGCAGAGCCGATCCAAGAGGGGCACCGAGGATGAGGAG  780
  93 HisArgAlaGluThrGlnGluGlnGlnSerArgSerLysArgGlyThrGluAspGluGlu  113

781 GCCAAGGGCGTGCAGCAGTATGTGCCTGAGGAGTGGGCGGAGTACCCCCGGCCCATTCAC  840
 113 AlaLysGlyValGlnGlnTyrValProGluGluTrpAlaGluTyrProArgProIleHis  133

841 CCTGCTGGCCTGCAGCCAACCAAGCCCTTGGTGGCCACCAGCCCTAACCCCGACAAGGAT  900
 133 ProAlaGlyLeuGlnProThrLysProLeuValAlaThrSerProAsnProAspLysAsp  153

901 GGGGGCACCCCAGACAGTGGGCAGGAACTGAGGGGCAATCTGACAGGGGCACCAGGGCAG  960
 153 GlyGlyThrProAspSerGlyGlnGluLeuArgGlyAsnLeuThrGlyAlaProGlyGln  173

961 AGGCTACAGATCCAGAACCCCCTGTATCCGGTGACCGAGAGCTCCTACAGTGCCTATGCC 1020
 173 ArgLeuGlnIleGlnAsnProLeuTyrProValThrGluSerSerTyrSerAlaTyrAla  193

1021 ATCATGCTTCTGGCGCTGGTGGTGTTTGCGGTGGGCATTGTGGGCAACCTGTCGGTCATG 1080
 193 IleMetLeuLeuAlaLeuValValPheAlaValGlyIleValGlyAsnLeuSerValMet  213

1081 TGCATCGTGTGGCACAGCTACTACCTGAAGAGCGCCTGGAACTCCATCCTTGCCAGCCTG 1140
 213 CysIleValTrpHisSerTyrTyrLeuLysSerAlaTrpAsnSerIleLeuAlaSerLeu  233

1141 GCCCTCTGGGATTTTCTGGTCCTCTTTTTCTGCCTCCCTATTGTCATCTTCAACGAGATC 1200
 233 AlaLeuTrpAspPheLeuValLeuPhePheCysLeuProIleValIlePheAsnGluIle  253

1201 ACCAAGCAGAGGCTACTGGGTGACGTTTCTTGTCGTGCCGTGCCCTTCATGGAGGTCTCC 1260
 253 ThrLysGlnArgLeuLeuGlyAspValSerCysArgAlaValProPheMetGluValSer  273

1261 TCTCTGGGAGTCACGACTTTCAGCCTCTGTGCCCTGGGCATTGACCGCTTCCACGTGGCC 1320
 273 SerLeuGlyValThrThrPheSerLeuCysAlaLeuGlyIleAspArgPheHisValAla  293

1321 ACCAGCACCCTGCCCAAGGTGAGGCCCATCGAGCGGTGCCAATCCATCCTGGCCAAGTTG 1380
 293 ThrSerThrLeuProLysValArgProIleGluArgCysGlnSerIleLeuAlaLysLeu  313

1381 GCTGTCATCTGGGTGGGCTCCATGACGCTGGCTGTGCCTGAGCTCCTGCTGTGGCAGCTG 1440
 313 AlaValIleTrpValGlySerMetThrLeuAlaValProGluLeuLeuLeuTrpGlnLeu  333
```

FIG. 3B

```
1441 GCACAGGAGCCTGCCCCCACCATGGGCACCCTGGACTCATGCATCATGAAACCCTCAGCC 1500
 333 AlaGlnGluProAlaProThrMetGlyThrLeuAspSerCysIleMetLysProSerAla  353

1501 AGCCTGCCCGAGTCCCTGTATTCACTGGTGATGACCTACCAGAACGCCCGCATGTGGTGG 1560
 353 SerLeuProGluSerLeuTyrSerLeuValMetThrTyrGlnAsnAlaArgMetTrpTrp  373

1561 TACTTTGGCTGCTACTTCTGCCTGCCCATCCTCTTCACAGTCACCTGCCAGCTGGTGACA 1620
 373 TyrPheGlyCysTyrPheCysLeuProIleLeuPheThrValThrCysGlnLeuValThr  393

1621 TGGCGGGTGCGAGGCCCTCCAGGGAGGAAGTCAGAGTGCAGGGCCAGCAAGCACGAGCAG 1680
 393 TrpArgValArgGlyProProGlyArgLysSerGluCysArgAlaSerLysHisGluGln  413

1681 TGTGAGAGCCAGCTCAACAGCACCGTGGTGGGCCTGACCGTGGTCTACGCCTTCTGCACC 1740
 413 CysGluSerGlnLeuAsnSerThrValValGlyLeuThrValValTyrAlaPheCysThr  433

1741 CTCCCAGAGAACGTCTGCAACATCGTGGTGGCCTACCTCTCCACCGAGCTGACCCGCCAG 1800
 433 LeuProGluAsnValCysAsnIleValValAlaTyrLeuSerThrGluLeuThrArgGln  453

1801 ACCCTGGACCTCCTGGGCCTCATCAACCAGTTCTCCACCTTCTTCAAGGGCGCCATCACC 1860
 453 ThrLeuAspLeuLeuGlyLeuIleAsnGlnPheSerThrPhePheLysGlyAlaIleThr  473

1861 CCAGTGCTGCTCCTTTGCATCTGCAGGCCGCTGGGCCAGGCCTTCCTGGACTGCTGCTGC 1920
 473 ProValLeuLeuLeuCysIleCysArgProLeuGlyGlnAlaPheLeuAspCysCysCys  493

1921 TGCTGCTGCTGTGAGGAGTGCGGCGGGGCTTCGGAGGCCTCTGCTGCCAATGGGTCGGAC 1980
 493 CysCysCysCysGluGluCysGlyGlyAlaSerGluAlaSerAlaAlaAsnGlySerAsp  513

1981 AACAAGCTCAAGACCGAGGTGTCCTCTTCCATCTACTTCCACAAGCCCAGGGAGTCACCC 2040
 513 AsnLysLeuLysThrGluValSerSerSerIleTyrPheHisLysProArgGluSerPro  533

2041 CCACTCCTGCCCCTGGGCACACCTTGCTGAGGCCCCAGTA                     2080
 533 ProLeuLeuProLeuGlyThrProCys***                               543
```

FIG. 3C

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 481 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Arg Trp Leu Trp Pro Leu Ala Val Ser Leu Ala Val Ile Leu Ala
 1               5                  10                  15

Val Gly Leu Ser Arg Val Ser Gly Gly Ala Pro Leu His Leu Gly Arg
            20                  25                  30
```

-continued

```
His Arg Ala Glu Thr Gln Glu Gln Ser Arg Ser Lys Arg Gly Thr
         35                  40                  45
Glu Asp Glu Glu Ala Lys Gly Val Gln Gln Tyr Val Pro Glu Trp
 50                  55                  60
Ala Glu Tyr Pro Arg Pro Ile His Pro Ala Gly Leu Gln Pro Thr Lys
 65                  70                  75                  80
Pro Leu Val Ala Thr Ser Pro Asn Pro Asp Lys Asp Gly Thr Pro
                 85                  90                  95
Asp Ser Gly Gln Glu Leu Arg Gly Asn Leu Thr Gly Ala Pro Gly Gln
                100                 105                 110
Arg Leu Gln Ile Gln Asn Pro Leu Tyr Pro Val Thr Glu Ser Ser Tyr
                115                 120                 125
Ser Ala Tyr Ala Ile Met Leu Leu Ala Leu Val Val Phe Ala Val Gly
        130                 135                 140
Ile Val Gly Asn Leu Ser Val Met Cys Ile Val Trp His Ser Tyr Tyr
145                 150                 155                 160
Leu Lys Ser Ala Trp Asn Ser Ile Leu Ala Ser Leu Ala Leu Trp Asp
                165                 170                 175
Phe Leu Val Leu Phe Phe Cys Leu Pro Ile Val Ile Phe Asn Glu Ile
                180                 185                 190
Thr Lys Gln Arg Leu Leu Gly Asp Val Ser Cys Arg Ala Val Pro Phe
        195                 200                 205
Met Glu Val Ser Ser Leu Gly Val Thr Thr Phe Ser Leu Cys Ala Leu
 210                 215                 220
Gly Ile Asp Arg Phe His Val Ala Thr Ser Thr Leu Pro Lys Val Arg
225                 230                 235                 240
Pro Ile Glu Arg Cys Gln Ser Ile Leu Ala Lys Leu Ala Val Ile Trp
                245                 250                 255
Val Gly Ser Met Thr Leu Ala Val Pro Glu Leu Leu Leu Trp Gln Leu
        260                 265                 270
Ala Gln Glu Pro Ala Pro Thr Met Gly Thr Leu Asp Ser Cys Ile Met
        275                 280                 285
Lys Pro Ser Ala Ser Leu Pro Glu Ser Leu Tyr Ser Leu Val Met Thr
 290                 295                 300
Tyr Gln Asn Ala Arg Met Trp Trp Tyr Phe Gly Cys Tyr Phe Cys Leu
305                 310                 315                 320
Pro Ile Leu Phe Thr Val Thr Cys Gln Leu Val Thr Trp Arg Val Arg
                325                 330                 335
Gly Pro Pro Gly Arg Lys Ser Glu Cys Arg Ala Ser Lys His Glu Gln
                340                 345                 350
Cys Glu Ser Gln Leu Asn Ser Thr Val Val Gly Leu Thr Val Val Tyr
        355                 360                 365
Ala Phe Cys Thr Leu Pro Glu Asn Val Cys Asn Ile Val Val Ala Tyr
        370                 375                 380
Leu Ser Thr Glu Leu Thr Arg Gln Thr Leu Asp Leu Leu Gly Leu Ile
385                 390                 395                 400
Asn Gln Phe Ser Thr Phe Phe Lys Gly Ala Ile Thr Pro Val Leu Leu
                405                 410                 415
Leu Cys Ile Cys Arg Pro Leu Gly Gln Ala Phe Leu Asp Cys Cys Cys
                420                 425                 430
Cys Cys Cys Cys Glu Glu Cys Gly Gly Ala Ser Glu Ala Ser Ala Ala
        435                 440                 445
Asn Gly Ser Asp Asn Lys Leu Lys Thr Glu Val Ser Ser Ser Ile Tyr
```

-continued

```
            450                 455                 460
Phe His Lys Pro Arg Glu Ser Pro Pro Leu Leu Pro Leu Gly Thr Pro
465                 470                 475                 480

Cys (2) INFORMATION FOR SEQ ID NO:2:

(i) SEQUENCE CHARACTERISTICS:
        (A) LENGTH: 542 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Cys Pro Ala Glu Gly Pro Ala Arg Pro Val Ala Gly Gly Trp Glu
1               5                   10                  15

Gly Gly Gln Ala Ser Asp Ala Arg Arg Leu Thr Gly Gly Gly Ser Ser
                20                  25                  30

Arg Pro Ala Ala Ser Leu Glu Pro Ser Ser Trp Ala Pro Cys Thr His
            35                  40                  45

Leu Leu Phe Leu Gly Trp Leu Ser Pro Ala His Pro Ala Met Arg Trp
        50                  55                  60

Leu Trp Pro Leu Ala Val Ser Leu Ala Val Ile Leu Ala Val Gly Leu
65                  70                  75                  80

Ser Arg Val Ser Gly Gly Ala Pro Leu His Leu Gly Arg His Arg Ala
                85                  90                  95

Glu Thr Gln Glu Gln Gln Ser Arg Ser Lys Arg Gly Thr Glu Asp Glu
            100                 105                 110

Glu Ala Lys Gly Val Gln Gln Tyr Val Pro Glu Glu Trp Ala Glu Tyr
        115                 120                 125

Pro Arg Pro Ile His Pro Ala Gly Leu Gln Pro Thr Lys Pro Leu Val
    130                 135                 140

Ala Thr Ser Pro Asn Pro Asp Lys Asp Gly Gly Thr Pro Asp Ser Gly
145                 150                 155                 160

Gln Glu Leu Arg Gly Asn Leu Thr Gly Ala Pro Gly Gln Arg Leu Gln
                165                 170                 175

Ile Gln Asn Pro Leu Tyr Pro Val Thr Glu Ser Ser Tyr Ser Ala Tyr
            180                 185                 190

Ala Ile Met Leu Leu Ala Leu Val Val Phe Ala Val Gly Ile Val Gly
        195                 200                 205

Asn Leu Ser Val Met Cys Ile Val Trp His Ser Tyr Tyr Leu Lys Ser
    210                 215                 220

Ala Trp Asn Ser Ile Leu Ala Ser Leu Ala Leu Trp Asp Phe Leu Val
225                 230                 235                 240

Leu Phe Phe Cys Leu Pro Ile Val Ile Phe Asn Glu Ile Thr Lys Gln
                245                 250                 255

Arg Leu Leu Gly Asp Val Ser Cys Arg Ala Val Pro Phe Met Glu Val
            260                 265                 270

Ser Ser Leu Gly Val Thr Thr Phe Ser Leu Cys Ala Leu Gly Ile Asp
        275                 280                 285

Arg Phe His Val Ala Thr Ser Thr Leu Pro Lys Val Arg Pro Ile Glu
    290                 295                 300

Arg Cys Gln Ser Ile Leu Ala Lys Leu Ala Val Ile Trp Val Gly Ser
305                 310                 315                 320
```

```
Met Thr Leu Ala Val Pro Glu Leu Leu Trp Gln Leu Ala Gln Glu
            325                 330                 335

Pro Ala Pro Thr Met Gly Thr Leu Asp Ser Cys Ile Met Lys Pro Ser
            340                 345                 350

Ala Ser Leu Pro Glu Ser Leu Tyr Ser Leu Val Met Thr Tyr Gln Asn
            355                 360                 365

Ala Arg Met Trp Trp Tyr Phe Gly Cys Tyr Phe Cys Leu Pro Ile Leu
        370                 375                 380

Phe Thr Val Thr Cys Gln Leu Val Thr Trp Arg Val Arg Gly Pro Pro
385                 390                 395                 400

Gly Arg Lys Ser Glu Cys Arg Ala Ser Lys His Glu Gln Cys Glu Ser
            405                 410                 415

Gln Leu Asn Ser Thr Val Val Gly Leu Thr Val Val Tyr Ala Phe Cys
            420                 425                 430

Thr Leu Pro Glu Asn Val Cys Asn Ile Val Val Ala Tyr Leu Ser Thr
            435                 440                 445

Glu Leu Thr Arg Gln Thr Leu Asp Leu Leu Gly Leu Ile Asn Gln Phe
    450                 455                 460

Ser Thr Phe Phe Lys Gly Ala Ile Thr Pro Val Leu Leu Cys Ile
465                 470                 475                 480

Cys Arg Pro Leu Gly Gln Ala Phe Leu Asp Cys Cys Cys Cys Cys
                485                 490                 495

Cys Glu Glu Cys Gly Gly Ala Ser Glu Ala Ser Ala Ala Asn Gly Ser
                500                 505                 510

Asp Asn Lys Leu Lys Thr Glu Val Ser Ser Ser Ile Tyr Phe His Lys
            515                 520                 525

Pro Arg Glu Ser Pro Pro Leu Leu Pro Leu Gly Thr Pro Cys
            530                 535                 540

(2) INFORMATION FOR SEQ ID NO:3:

(i) SEQUENCE CHARACTERISTICS:
        (A) LENGTH: 1443 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGCGGTGGC TGTGGCCCCT GGCTGTCTCT CTTGCTGTGA TTTTGGCTGT GGGGCTAAGC      60

AGGGTCTCTG GGGGTGCCCC CCTGCACCTG GGCAGGCACA GAGCCGAGAC CCAGGAGCAG     120

CAGAGCCGAT CCAAGAGGGG CACCGAGGAT GAGGAGGCCA AGGGCGTGCA GCAGTATGTG     180

CCTGAGGAGT GGGCGGAGTA CCCCCGGCCC ATTCACCCTG CTGGCCTGCA GCCAACCAAG     240

CCCTTGGTGG CCACCAGCCC TAACCCCGAC AAGGATGGGG CACCCCAGA CAGTGGGCAG      300

GAACTGAGGG GCAATCTGAC AGGGGCACCA GGGCAGAGGC TACAGATCCA GAACCCCCTG     360

TATCCGGTGA CCGAGAGCTC CTACAGTGCC TATGCCATCA TGCTTCTGGC GCTGGTGGTG     420

TTTGCGGTGG GCATTGTGGG CAACCTGTCG GTCATGTGCA TCGTGTGGCA CAGCTACTAC     480

CTGAAGAGCG CCTGGAACTC CATCCTTGCC AGCCTGGCCC TCTGGGATTT TCTGGTCCTC     540

TTTTTCTGCC TCCCTATTGT CATCTTCAAC GAGATCACCA AGCAGAGGCT ACTGGGTGAC     600

GTTTCTTGTC GTGCCGTGCC CTTCATGGAG GTCTCCTCTC TGGGAGTCAC GACTTTCAGC     660

CTCTGTGCCC TGGGCATTGA CCGCTTCCAC GTGGCCACCA GCACCCTGCC CAAGGTGAGG     720
```

```
CCCATCGAGC GGTGCCAATC CATCCTGGCC AAGTTGGCTG TCATCTGGGT GGGCTCCATG    780
ACGCTGGCTG TGCCTGAGCT CCTGCTGTGG CAGCTGGCAC AGGAGCCTGC CCCCACCATG    840
GGCACCCTGG ACTCATGCAT CATGAAACCC TCAGCCAGCC TGCCCGAGTC CCTGTATTCA    900
CTGGTGATGA CCTACCAGAA CGCCCGCATG TGGTGGTACT TTGGCTGCTA CTTCTGCCTG    960
CCCATCCTCT TCACAGTCAC CTGCCAGCTG GTGACATGGC GGGTGCGAGG CCCTCCAGGG   1020
AGGAAGTCAG AGTGCAGGGC CAGCAAGCAC GAGCAGTGTG AGAGCCAGCT CAACAGCACC   1080
GTGGTGGGCC TGACCGTGGT CTACGCCTTC TGCACCCTCC CAGAGAACGT CTGCAACATC   1140
GTGGTGGCCT ACCTCTCCAC CGAGCTGACC CGCCAGACCC TGGACCTCCT GGGCCTCATC   1200
AACCAGTTCT CCACCTTCTT CAAGGGCGCC ATCACCCCAG TGCTGCTCCT TTGCATCTGC   1260
AGGCCGCTGG GCCAGGCCTT CCTGGACTGC TGCTGCTGCT GCTGCTGTGA GGAGTGCGGC   1320
GGGGCTTCGG AGGCCTCTGC TGCCAATGGG TCGGACAACA AGCTCAAGAC CGAGGTGTCC   1380
TCTTCCATCT ACTTCCACAA GCCCAGGGAG TCACCCCCAC TCCTGCCCCT GGGCACACCT   1440
TGC                                                                1443

(2) INFORMATION FOR SEQ ID NO:4:

(i) SEQUENCE CHARACTERISTICS:
        (A) LENGTH: 1626 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATGTGTCCAG CAGAGGGCCC TGCCCGGCCT GTGGCCGGAG CTGGGAGGG AGGGCAGGCG     60
AGTGATGCCA GACGCCTGAC TGGAGGCGGA TCCAGCCGGC CAGCTGCCTC TCTGGAGCCC   120
AGCTCTTGGG CCCCCTGTAC TCACCTGCTC TTCCTGGGCT GGCTGTCTCC TGCTCATCCA   180
GCCATGCGGT GGCTGTGGCC CCTGGCTGTC TCTCTTGCTG TGATTTTGGC TGTGGGGCTA   240
AGCAGGGTCT CTGGGGGTGC CCCCCTGCAC CTGGGCAGGC ACAGAGCCGA GACCCAGGAG   300
CAGCAGAGCC GATCCAAGAG GGGCACCGAG GATGAGGAGG CCAAGGGCGT GCAGCAGTAT   360
GTGCCTGAGG AGTGGGCGGA GTACCCCCGG CCCATTCACC CTGCTGGCCT GCAGCCAACC   420
AAGCCCTTGG TGGCCACCAG CCCTAACCCC GACAAGGATG GGGGCACCCC AGACAGTGGG   480
CAGGAACTGA GGGGCAATCT GACAGGGGCA CCAGGGCAGA GGCTACAGAT CCAGAACCCC   540
CTGTATCCGG TGACCGAGAG CTCCTACAGT GCCTATGCCA TCATGCTTCT GGCGCTGGTG   600
GTGTTTGCGG TGGGCATTGT GGGCAACCTG TCGGTCATGT GCATCGTGTG GCACAGCTAC   660
TACCTGAAGA GCGCCTGGAA CTCCATCCTT GCCAGCCTGG CCCTCTGGGA TTTTCTGGTC   720
CTCTTTTTCT GCCTCCCTAT TGTCATCTTC AACGAGATCA CCAAGCAGAG GCTACTGGGT   780
GACGTTTCTT GTCGTGCCGT GCCCTTCATG GAGGTCTCCT CTCTGGGAGT CACGACTTTC   840
AGCCTCTGTG CCCTGGGCAT TGACCGCTTC CACGTGGCCA CCAGCACCCT GCCCAAGGTG   900
AGGCCCATCG AGCGGTGCCA ATCCATCCTG GCCAAGTTGG CTGTCATCTG GGTGGGCTCC   960
ATGACGCTGG CTGTGCCTGA GCTCCTGCTG TGGCAGCTGG CACAGGAGCC TGCCCCCACC  1020
ATGGGCACCC TGGACTCATG CATCATGAAA CCCTCAGCCA GCCTGCCCGA GTCCCTGTAT  1080
TCACTGGTGA TGACCTACCA GAACGCCCGC ATGTGGTGGT ACTTTGGCTG CTACTTCTGC  1140
CTGCCCATCC TCTTCACAGT CACCTGCCAG CTGGTGACAT GGCGGGTGCG AGGCCCTCCA  1200
```

```
GGGAGGAAGT CAGAGTGCAG GGCCAGCAAG CACGAGCAGT GTGAGAGCCA GCTCAACAGC    1260

ACCGTGGTGG GCCTGACCGT GGTCTACGCC TTCTGCACCC TCCCAGAGAA CGTCTGCAAC    1320

ATCGTGGTGG CCTACCTCTC CACCGAGCTG ACCCGCCAGA CCCTGGACCT CCTGGGCCTC    1380

ATCAACCAGT TCTCCACCTT CTTCAAGGGC GCCATCACCC CAGTGCTGCT CCTTTGCATC    1440

TGCAGGCCGC TGGGCCAGGC CTTCCTGGAC TGCTGCTGCT GCTGCTGCTG TGAGGAGTGC    1500

GGCGGGGCTT CGGAGGCCTC TGCTGCCAAT GGGTCGGACA ACAAGCTCAA GACCGAGGTG    1560

TCCTCTTCCA TCTACTTCCA CAAGCCCAGG GAGTCACCCC CACTCCTGCC CCTGGGCACA    1620

CCTTGC                                                               1626

(2) INFORMATION FOR SEQ ID NO:5:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TGCAATCCAT CCTGGCCAAG TTGGCTGTCA TCTGGGTGGG CTCCATGACG CTGGCTGTGC     60

CTGAGCTCCT GCTGTGGCAG CTGGCACAGG AGCCTGCCCC CACCATGGGC ACCCTGGACT    120

CATGCATCAT GAAACCCTCA GCCAGCCTGC CCGAGTCCCT GTATTCACTG GTGATGACCT    180

ACCAGAACGC CCGCATGTGG TGGTACTTTG GCTGCTACTT CTGCCTGCCC ATCCTCTTCA    240

CAGTCACCTG CCAGCTGGTG ACATGGCGGG TGCGAGGCCC TCCAGGGAGG AAGTCAGAGT    300

GCAGGGCCAG CAAGCACGAG CAGTGTGAGA GCCAGCTCAA CAGCACCGTG GTGGGCCTGA    360

CCGTGGTCTA CGGCTTTTTG CAACCTTCCA GAGAACGTTT GCAACATCGT GGTGGGCTTA    420

CCTTTT                                                               426

(2) INFORMATION FOR SEQ ID NO:6:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AACAAGGGCC GTGGTCTACG NCTTCTGCAC CCTCCCANAG AACGTCTGCA ACATCGTGGT     60

GGCCTACCTC TCCACCGAGC TGACCCGCCA GNCCCTGGAC CTCCTGGGCC TCATCAACCA    120

GTTCTCCACC TTCTTCAAGG GCGCCATCAC CCCAGTGCTG CTCCTTTGCA TCTGCAGGCC    180

GCTGGGCCAG GCCTTCCTGG ACTGCTGCTG CTGCTGCTGC TGTNAGGAGT GCGGCGGGGC    240

TTCGGAGG                                                             248

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:7:

AAGTTGGCTG TCATCTGGGT GGGCTC         26

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TGAGCTCCTG CTGTGGCAGC TGGCACAG         28

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CATGCGGGCG TTCTGGTAGG TCATCAC         27

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GAAGAGGATG GGCAGGCAGA AGTAGCAG         28

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ATGAAGGGCA CGGCACGACA AGAAACG         27

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATGACAATAG GGAGGCAGAA AAAGAGG         27

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GTCGACGAGA TGTGTGAGGG CAGCAAAGAG TGC                    33

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TACTGGGGCC TCAGCAAGGT GTGCCCAG                          28

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GTCGACTGGC TGTCTCCTGC TCATCCAGCC AT                    32

HUMAN G-PROTEIN COUPLED RECEPTOR POLYNUCLEOTIDES

FIELD OF THE INVENTION

The present invention relates to novel G-protein coupled receptor proteins derived from a human brain, or salts thereof.

BACKGROUND OF THE INVENTION

Many hormones and neurotransmitters regulate functions in a living body through specific receptor proteins existing in a cell membrane. Many of these receptor proteins mediate signal transmission in a cell by activation of coupled guanine nucleotide-binding proteins (hereinafter, sometimes, referred to as G-proteins) and are generally called G-protein coupled receptor proteins or 7-transmembrane receptor proteins because they contain a common structure having seven transmembrane domains.

G-protein coupled receptor proteins exist on each functional cell surface of cells and internal organs of a living body and play very important roles as targets of molecules which regulate functions of the cells and internal organs of the living body, for example, hormones, neurotransmitters, physiologically active substances and the like.

To clarify the relation between substances which regulate elaborate functions in cells and internal organs of various living bodies and their specific receptor proteins, in particular, G-protein coupled receptor proteins provide a very important means for clarification of functional mechanisms of cells and internal organs of various living body as well as for development of drugs having close relation to such functional mechanisms. For example, in a central nerve system organ such as a brain, its physiological functions are controlled through regulation by many hormones, hormone-like substances, neurotransmitters, physiologically active substances or the like. In particular, neurotransmitters are found in numerous sites within a brain and regulate the physiological functions thought their corresponding receptor proteins.

However, it is supposed that many unknown neurotransmitters still exist in a brain and, as for their receptor proteins, many structures of cDNAs encoding such proteins have not yet been reported. In addition, it is still unknown if there are subtypes of known receptor proteins.

Also, to clarify the relation between substances which regulate elaborate functions in a brain and their specific receptor proteins provides a very important means for development of drugs. Further, for screening for agonists and antagonists to receptor proteins, efficiently, in development of drugs, it is required to clarify functional mechanisms of receptor protein genes expressed in a brain and to express them in a suitable expression system.

Recently, as a means for analyzing genes expressed in a living body, random analysis of cDNA sequences has been studied actively. The sequences of cDNA fragments thus obtained have been registered with data bases as Expressed Sequence Tags (ESTs) and are publicly available. However, for many of ESTs, it is difficult to deduce their functions from their sequential information only. For example, although two ESTs, accession No. T08099 (SEQ ID NO: 5) and No. T27053 (SEQ ID NO: 6), have been registered with the data base, NCBI dbEST, their functions are not clarified.

OBJECTS OF THE INVENTION

One object of the present invention is to provide novel G-protein coupled receptor proteins derived from a human brain, their partial peptides and their salts.

Another object of the present invention is to provide isolated DNA comprising DNA encoding the G-protein coupled receptor proteins or their partial peptides.

A further object of the present invention is to provide a recombinant vector comprising the DNA and a transformant having the recombinant vector.

A further object of the present invention is to provide a process for preparing the G-protein coupled receptor proteins or their salts.

Still another object of the present invention is to provide a method for determining ligands to the G-protein coupled receptors.

Still another object of the present invention is to provide a method for screening for receptor-agonists or antagonists to the G-protein coupled receptor proteins, a kit for screening for the receptor-agonists or antagonists, the receptor-agonists or antagonists obtained by the screening and a pharmaceutical composition comprising at least one of the receptor-agonists or antagonists.

Yet another object of the present invention is to provide antibodies against the G-protein coupled receptor proteins, their partial peptides or salts.

These objects as well as other objects and advantages of the present invention will become apparent to those skilled in the art from the following description with reference to the accompanying drawings.

BRIEF EXPLANATION OF DRAWINGS

FIG. 1 is a nucleotide sequence (SEQ ID NO:3) encoding the human G-protein coupled receptor protein (short form) of the present invention obtained in Example 1 hereinafter and its amino acid sequence (SEQ ID NO:1) deduced from the nucleotide sequence.

FIG. 3 is a nucleotide sequence (SEQ ID NO:4) encoding the human G-protein coupled receptor protein (long form) of the present invention obtained in Example 1 hereinafter and its amino acid sequence (SEQ ID NO:2) deduced from the nucleotide sequence.

SUMMARY OF THE INVENTION

Figure 2:
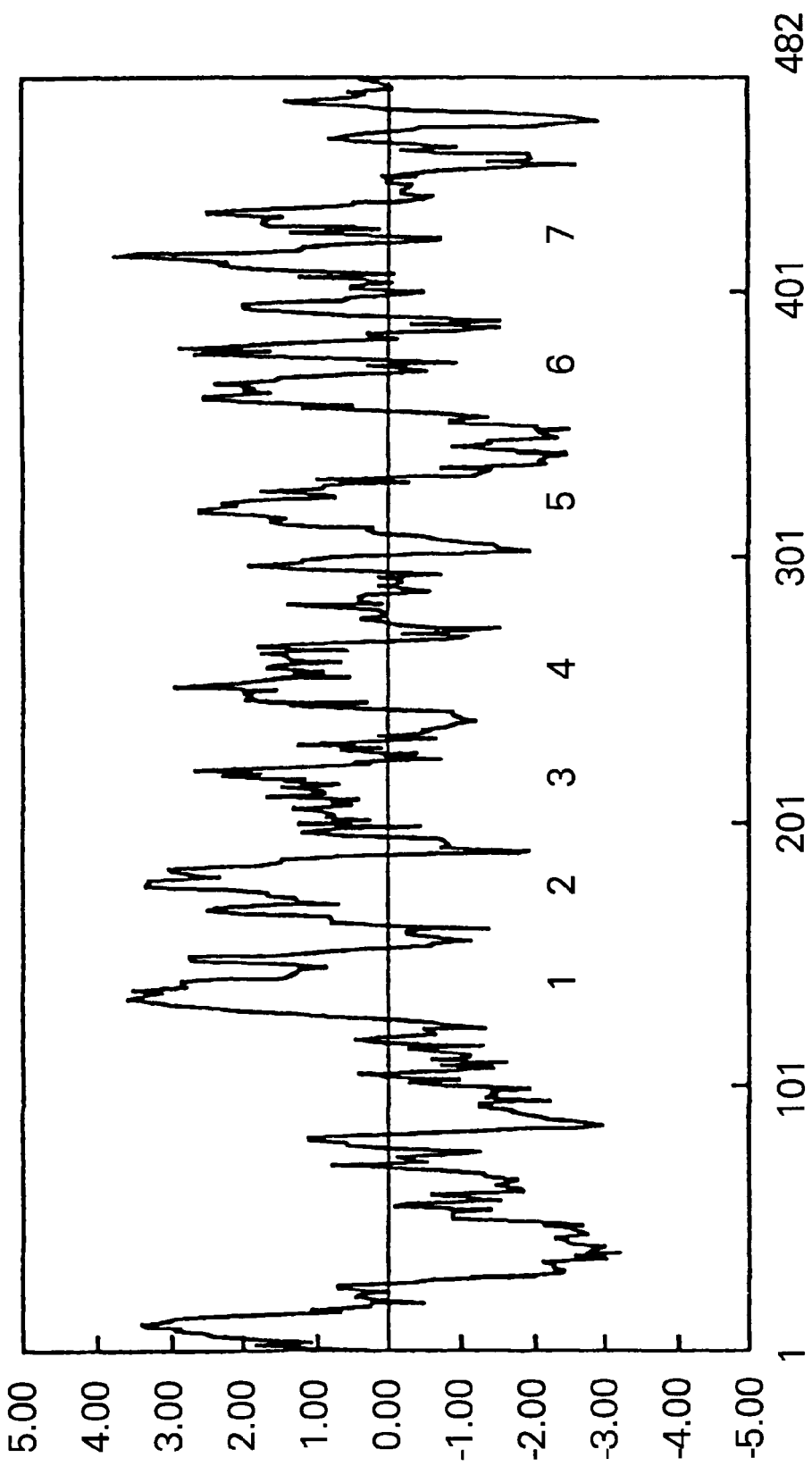
FIG. 2 is a graph illustrating hydrophobic plotting of the human G-protein coupled receptor protein (short form) of the present invention prepared based on the amino acid sequence of FIG. 1. The parts represented by 1 to 7 are hydrophobic domains.

As a result of an intensive study, the present inventors have succeeded in isolation of cDNAs encoding two kinds of G-protein coupled receptor proteins derived from human fetal brain and human adult brain based on two kinds of publicly available EST information registered with a data base whose functions are unknown, and have succeeded in analysis of the entire nucleotide sequences. When their amino acid sequences have been deduced from the nucleotide sequences, the first to the seventh transmembrane domains have been confirmed on hydrophobic plotting. Thus, the proteins encoded by these cDNAs have been confirmed to be 7-transmembrane type G-protein coupled receptor proteins. The present invention has been completed based on these findings.

That is, according to the present invention, there are provided:

(1) A G-protein coupled receptor protein which comprises the same or substantially the same amino acid sequence as that represented by SEQ ID NO: 1, or its salt;

(2) The G-protein coupled receptor protein of the above (1) which comprises the same or substantially the same amino acid sequence as that represented by SEQ ID NO: 2, or its salt;

(3) A partial peptide of the G-protein coupled receptor protein of the above (1) or its salt;

(4) An isolated DNA comprising DNA having a nucleotide sequence encoding the G-protein coupled receptor protein of the above (1);

(5) The isolated DNA of the above (4) having the nucleotide sequence represented by SEQ ID NO: 3;

(6) The isolated DNA of the above (4) having the nucleotide sequence represented by SEQ ID NO: 4;

(7) A recombinant vector comprising the DNA of the above (4);

(8) A transformant comprising the recombinant vector of the above (7);

(9) A process for preparing the G-protein coupled receptor protein of the above (1) or its salt which comprises cultivating the transformant of the above (8) to form the G-protein coupled receptor protein;

(10) A method for determining a ligand to the G-protein coupled receptor protein of the above (1) or its salt which comprises bringing the G-protein coupled receptor protein of the above (1) or its salt or the partial peptide of the above (3) or its salt into contact with a test compound;

(11) A method for screening for compounds which alter binding of a ligand to the G-protein coupled receptor protein of the above (1) or its salt, or their salts which comprises comparing (i) ligand binding upon bringing the G-protein coupled receptor protein of the above (1) or its salt or the partial peptide of the above (3) or its salt into contact with the ligand, and (ii) that upon bringing the G-protein coupled receptor protein of the above (1) or its salt or the partial peptide of the above (3) or its salt into contact with the ligand and a test compound;

(12) A kit for screening for compounds which alter binding of a ligand to the G-protein coupled receptor protein of the above (1) or its salt, or their salts which comprises as an essential component the G-protein coupled receptor protein of the above (1) or its salt or the partial peptide of the above (3) or its salt;

(13) The compounds which alter ligand binding to the G-protein coupled receptor protein of the above (1) or its salt obtained by the screening method of the above (11) or the kit of the above (12), or their salts; and

(14) An antibody against the G-protein coupled receptor protein of the above (1) or its salt or the partial peptide of the above (3) or its salt.

More specifically, the present invention provides:

(15) The G-protein coupled receptor protein of the above (1) or its salt, wherein the protein comprises the amino acid sequence represented by SEQ ID NO: 1, a variant of the amino acid sequence represented by SEQ ID NO: 1 having a deletion of one or more, preferably about 1 to about 30, more preferably about 1 to about 10 amino acids, a variant of the amino acid sequence represented by SEQ ID NO: 1 having an addition of one or more, preferably about 1 to about 30, more preferably about 1 to about 10 amino acids, or a variant of the amino acid sequence represented by SEQ ID NO: 1 having a substitution of one or more, preferably about 1 to about 30, more preferably about 1 to about 10 amino acids;

(16) The G-protein coupled receptor protein of the above (2) or its salt, wherein the protein comprises the amino acid sequence represented by SEQ ID NO: 2, a variant of the amino acid sequence represented by SEQ ID NO: 2 having a deletion of one or more, preferably about 1 to about 30, more preferably about 1 to about 10 amino acids, a variant of the amino acid sequence represented by SEQ ID NO: 2 having an addition of one or more, preferably about 1 to about 30, more preferably about 1 to about 10 amino acids, or a variant of the amino acid sequence represented by SEQ ID NO: 2 having a substitution of one or more, preferably about 1 to about 30, more preferably about 1 to about 10 amino acids;

(17) The method for determining a ligand of the above (10), wherein the ligand is angiotensin, bombesin, cannabinoid, cholecystokinin, glutamine, serotonin, melatonin, neuropeptide Y, opioid, purine, vasopressin, oxytocin, PACAP, secretin, glucagon, calcitonin, adrenomedullin, somatostatin, GHRH, CRF, ACTH, GRP, PTH, VIP (vasoactive intestinal and related polypeptides), dopamine, motilin, amylin, bradykinin, CGRP (calcitonin gene related proteins), leukotriene, pancreastacin, prostaglandin, thromboxane, adenosine, adrenalin, α or β-chemokine (e.g., IL-8, GROα, GROβ, GROγ, NAP-2, ENA-78, PF4, IP10, GCP-2, MCP-1, HC14, MCP-3, I-309, MIP-1α, MIP-1β, RANTES, etc.), endothelin, enterogastrin, histamine, neurotensin, TRH, pancreatic polypeptides or gallamine;

(18) A method for screening for compounds which alter binding of a ligand to the G-protein coupled receptor protein or its salt of the above (1), or their salts which comprises labeling the ligand, and measuring and comparing (i) an amount of the labeled ligand bound to the G-protein coupled receptor protein of the above (1) or its salt or the partial peptide of the above (3) or its salt upon bringing the protein of the above (1), the partial peptide of the above (3) or a salt thereof into contact with the labeled ligand, and (ii) that upon bringing the protein of the above (1), the partial peptide of the above (3) or a salt thereof into contact with the labeled ligand and a test compound;

(19) A method for screening for compounds which alter binding of a ligand to the G-protein coupled receptor protein of the above (1) or its salt, or their salts which comprises labeling the ligand, and measuring and comparing (i) an amount of the labeled ligand bound to cells containing the G-protein coupled receptor protein of the above (1) upon bringing the labeled ligand into contact with the cells with (ii) that upon bringing the labeled ligand and a test compound into contact with the cells;

(20) A method for screening for compounds which alter binding of a ligand to the G-protein coupled receptor protein of the above (1) or its salt, or their salts which comprises labeling the ligand, and measuring and comparing (i) an amount of the labeled ligand bound to a membrane fraction of cells containing the G-protein coupled receptor protein of the above (1) upon bringing the labeled ligand into contact with the cell membrane fraction, and (ii) that upon bringing the labeled ligand and a test compound into contact with the cell membrane fraction;

(21) A method for screening for compounds which alter binding of a ligand to the G-protein coupled receptor protein of the above (1) or its salt, or their salts which comprises labeling the ligand, and measuring and comparing (i) an amount of the labeled ligand bound to the G-protein coupled receptor protein expressed on the cell membrane of the transformant of the above (8) by cultivating the transformant upon bringing the labeled ligand into contact with the expressed G-protein coupled receptor protein, and (ii) that upon bringing the labeled ligand and a test compound into contact with the expressed G-protein coupled receptor protein;

(22) A method for screening for compounds which alter binding of a ligand to the G-protein coupled receptor protein of the above (1) or its salt, or their salts which comprises measuring and comparing (i) a cell stimulation activity mediated by the G-protein coupled receptor protein upon bringing a compound which activates the G-protein coupled receptor protein of the above (1) or its salt into contact with cells containing the G-protein coupled receptor protein of the above (1), and (ii) that upon bringing the compound which activates the G-protein coupled receptor protein or its salt and a test compound into contact with the cells;

(23) A method for screening for compounds which alter binding of a ligand to the G-protein coupled receptor protein of the above (1) or its salt, or their salts which comprises measuring and comparing (i) a cell stimulation activity mediated by the G-protein coupled receptor protein upon bringing a compound which activates the G-protein coupled receptor protein of the above (1) or its salt into contact with the G-protein coupled receptor protein expressed on the cell membrane of the transformant of the above (8) by cultivating the transformant, and (ii) that upon bringing the compound which activates the G-protein coupled receptor protein or its salt and a test compound into contact with the G-protein coupled receptor protein expressed on the cell membrane;

(24) The method for screening of the above (22) or (23), wherein the compound which activates the G-protein coupled receptor protein of the above (1) is angiotensin, bombesin, cannabinoid, cholecystokinin, glutamine, serotonin, melatonin, neuropeptide Y, opioid, purine, vasopressin, oxytocin, PACAP, secretin, glucagon, calcitonin, adrenomedullin, somatostatin, GHRH, CRF, ACTH, GRP, PTH, VIP (vasoactive intestinal and related polypeptides), dopamine, motilin, amylin, bradykinin, CGRP (calcitonin gene related proteins), leukotriene, pancreastacin, prostaglandin, thromboxane, adenosine, adrenalin, α or β-chemokine (e.g., IL-8, GROα, GROβ, GROγ, NAP-2, ENA-78, PF4, IP10, GCP-2, MCP-1, HC14, MCP-3, I-309, MIP-1α, MIP-1β, RANTES, etc.), endothelin, enterogastrin, histamine, neurotensin, TRH, pancreatic polypeptides or gallamine;

(25) Compounds which alter binding of a ligand to the G-protein coupled receptor protein of the above (1) or its salt obtained in any one of the method of screening of the above (11) and (18) or (24), or their salts;

(26) A pharmaceutical composition comprising the compound of the above (25) or its salt;

(27) The screening kit of the above (12) comprising cells containing the G-protein coupled receptor protein of the above (1);

(28) The screening kit of the above (12) comprising a membrane fraction of cells containing the G-protein coupled receptor protein of the above (1);

(29) The compound which alters ligand binding to the G-protein coupled receptor protein of the above (1) or its salt obtained by using the screening kit of the above (12), (27) or (28), or its salt;

(30) A pharmaceutical composition comprising the compound of the above (29) or its salt; and

(31) A method for determining the G-protein coupled receptor protein of the above (1), or its salt or the partial peptide of the above (3) or its salt which comprises bringing the antibody of the above (14) into contact with the G-protein coupled receptor protein of the above (1), the partial peptide of the above (3) or a salt thereof.

DETAILED DESCRIPTION OF THE INVENTION

The G-protein coupled receptor protein of the present invention (hereinafter sometimes abbreviated to "receptor protein") is the receptor protein which has the same or substantially the same amino acid sequence as that represented by SEQ ID NO: 1 (FIG. 1) and it may be the receptor protein having the same or substantially the same amino acid sequence as that represented by SEQ ID NO: 2 (FIG. 3). The amino acid sequence of SEQ ID NO: 2 is a variant of the amino acid sequence represented by SEQ ID NO: 1 having an addition of 61 amino acids at the N-terminal end of SEQ ID NO: 1.

The receptor protein of the present invention may be any peptide derived from any cells of a human being and another mammal (e.g., guinea pig, rat, mouse, chicken, rabbit, pig, sheep, cattle, monkey, etc.), for example, splenic cell, nerve cell, glia cell, β cell of pancreas, marrow cell, mesangial cell, Langerhans' cell, epidermic cell, epithelial cell, endothelial cell, fibroblast, fibrocyte, muscular cell, fat cell, immunocyte (e.g., macrophage, T cell, B cell, natural killer cell, mast cell, neutrophil, basophil, eosinophilic leukocyte, monocyte, etc.), megakaryocyte, synovial cell, chondrocyte, osteocyte, osteoblast, osteoclast, mammary gland cell, hepatocyte, or interstitial cells or precursor cells, stem cells or cancer cells thereof and the like; and any tissues containing such cells, for example, brain, various parts of the brain (e.g., olfactory bulb, amygdala, cerebral basal ganglia, hippocampus, thalamus, hypothalamus, substhanlamic nucleus, cerebral cortex, medulla, cerebellum, occipital pole, frontal lobe, putamen, caudate nucleus, corpus callosum, substantia nigra), spinal cord, pituitary, stomach, pancreas, kidney, liver, genital organs, thyroid gland, gallbladder, bone marrow, adrenal gland, skin, muscle, lung, digestive tract, blood vessel, heart, thymus, spleen, submandibular gland, peripheral blood, peripheral blood leukocyte, intestinal tract, prostate, testicle, testis, ovarium, placenta, uterus, bone, joint, small intestine, large intestine, skeletal muscle and the like, in particular, brain and various parts of the brain. And, the peptide may be a synthetic one.

The wording "the same or substantially the same as the amino acid sequence as that represented by SEQ ID NO: 1 or SEQ ID NO: 2" includes any protein which has at least about 70% homology, preferably at least about 80% homology, more preferably at least about 90% homology to the amino acid sequence represented by SEQ ID NO: 1 or SEQ ID NO: 2 and having substantially the same activity as that of the receptor protein comprising the amino acid sequence represented by SEQ ID NO: 1 or SEQ ID NO: 2.

Examples of substantially the same activity include ligand binding activity, signal information transmission activity and the like. The wording "substantially the same" means that the natures of their activities are equal to one another.

Therefore, quantitative factors such as degrees of ligand binding activity and signal information transmission activity may differ from one another.

Further, the receptor protein of the present invention may be a protein comprising a variant of the amino acid sequence represented by SEQ ID NO: 2 having a deletion of one or more, preferably about 1 to about 30, more preferably about 1 to about 10 amino acids, a variant of the amino acid sequence represented by SEQ ID NO: 2 having an addition of one or more, preferably about 1 to about 30, more preferably about 1 to about 10 amino acids, or a variant of the amino acid sequence represented by SEQ ID NO: 2 having a substitution of one or more, preferably about 1 to about 30, more preferably about 1 to about 10 amino acids.

More specifically, the receptor protein of the present invention includes, for example, the receptor protein comprising the amino acid sequence represented by SEQ ID: NO 1 derived from a human brain, or the G-protein coupled receptor protein comprising the amino acid sequence represented by SEQ ID: NO 2 derived from a human brain.

Furthermore, examples of the receptor protein of the present invention include variants of the above receptor protein, wherein the amino group of the N-terminal methionine residue of the above receptor protein is protected with a protecting group (e.g., acyl group having 1 to 6 carbon atoms such as formyl group, acetyl group, etc.); the N-terminal region of the above receptor protein is cleaved in a living body and the glutamyl group formed is pyroglutaminated; or a substituent (e.g., —OH, —COOH, amino group, imidazole group, indole group, guanidino group, etc.) on the side chain of an amino acid in the molecule of the above receptor protein is protected with a suitable protecting group (e.g., acyl group having 1 to 6 carbon atoms such as formyl group, acetyl group, etc.), or conjugated proteins of the above receptor protein such as glycoproteins having sugar chains.

The receptor protein of the present invention is represented by a conventional manner in peptide art. That is, the left hand end (amino terminal) is the N-terminal and the right hand end (carboxyl terminal) is the C-terminal. And, in the receptor protein of the present invention, a representative example thereof being the receptor protein comprising the amino acid sequence represented by SEQ ID NO: 1 or SEQ ID NO: 2, normally, the C-terminal is carboxyl group (—COOH) or carboxylate (—COO$^-$), but the C-terminal may be the amide (—CONH$_2$) or an ester (—COOR). Examples of R of the ester group include an alkyl group having 1 to 6 carbon atoms such as methyl, ethyl, n-propyl, isopropyl, n-butyl, etc., a cycloalkyl group having 3 to 8 carbon atoms such as cyclopentyl, cyclohexyl, etc., an aryl group having 6 to 12 carbon atoms such as phenyl, α-naphthyl, etc., an aralkyl having 7 to 14 carbon atoms such as a phenyl-$C_{1-2}$ alkyl group (e.g., benzyl, phenethyl, etc.), an α-naphthyl-$C_{1-2}$ alkyl group (e.g., α-naphthylmethyl, etc.) and the like. In addition, pivaloyloxymethyl ester or the like which is used widely as an ester for oral administration can also be used.

When the receptor protein of the present invention has a carboxyl group (or carboxylate) at a position other than the C-terminal, it may be amidated or esterified and such amide or ester is also included in the scope of the receptor protein of the present invention. The ester group may be the same group as that described with respect to the above C-terminal.

As the salt of the receptor protein of the present invention, in particular, a physiologically acceptable acid addition salt is preferred. Examples of the salt include those with inorganic acids (e.g., hydrochloric acid, phosphoric acid, hydrobromic acid, sulfuric acid, etc.) and those with organic acids (e.g., acetic acid, formic acid, propionic acid, fumaric acid, maleic acid, succinic acid, tartaric acid, citric acid, malic acid, oxalic acid, benzoic acid, methanesulfonic acid, benznesulfonic acid, etc.).

The receptor protein or its salt of the present invention can be prepared from the above-described cells and tissues of a human being or another mammal by a per se known purification method of proteins. Alternatively, the receptor protein or its salt of the present invention can be prepared by cultivating a transformant containing DNA encoding the receptor protein of the present invention or according to a peptide synthesis method as described hereinafter.

When it is produced from cells or tissues of a human being or another mammal, the cells or tissues are homogenized and then extracted with, for example, an acid. The extract can be purified and isolated by combining chromatographies such as reverse phase chromatography, ion exchange chromatography and the like.

Figure 4:
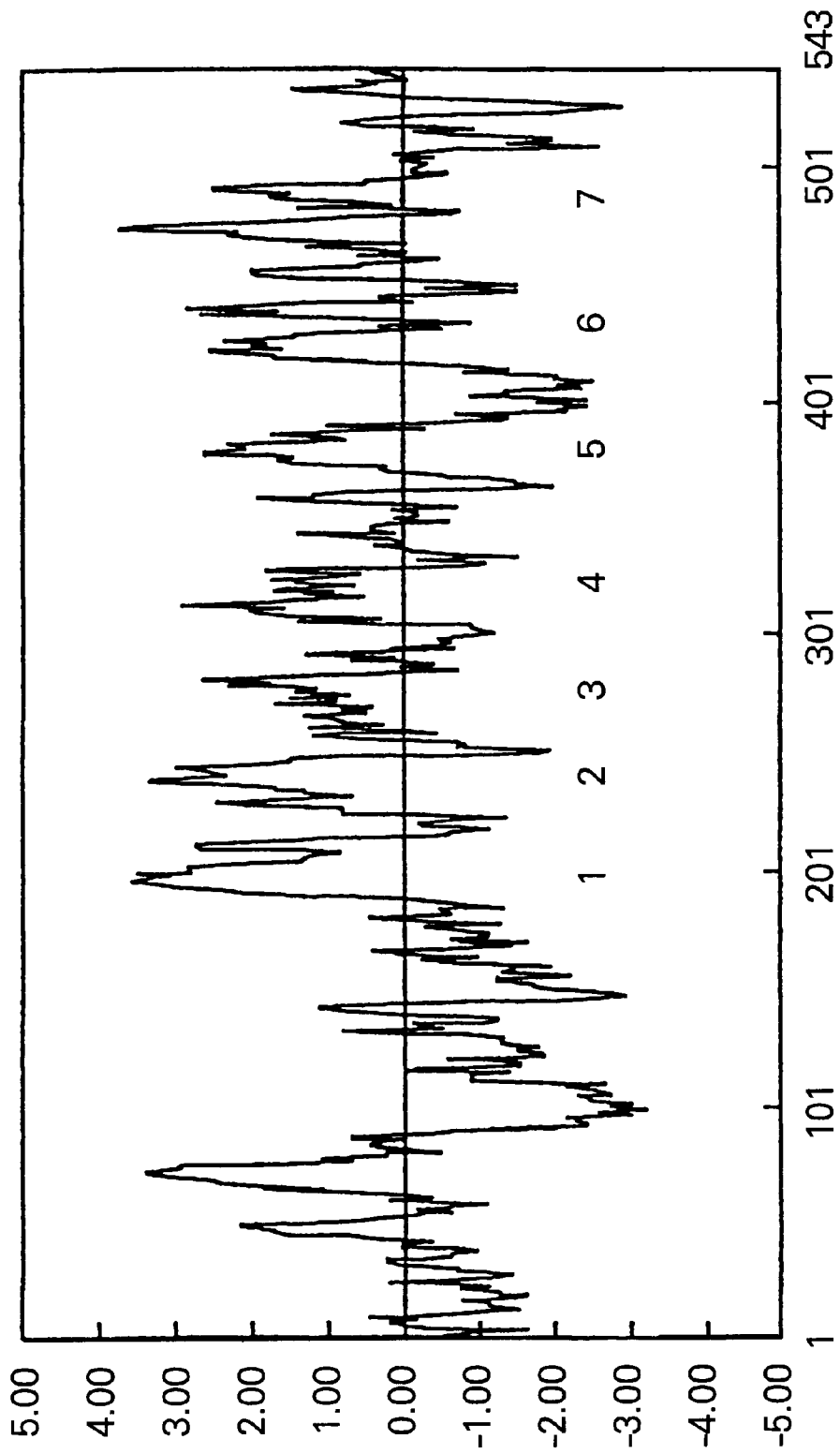
FIG. 4 is a graph illustrating hydrophobic plotting of the human G-protein coupled receptor protein (long form) of the present invention prepared based on the amino acid sequence of FIG. 1. The parts represented by 1 to 7 are hydrophobic domains.

As the partial peptide of the receptor protein (hereinafter sometimes abbreviated to "partial peptide") of the present invention, for example, a part of the receptor protein molecule of the present invention which is exposed to outside of a cell membrane or the like can be used. Specifically, the partial peptide of the receptor protein having the amino acid sequence represented by SEQ ID NO: 1 is a peptide containing the parts which have been analyzed to be extracellular domains (hydrophilic domains) in the hydrophobic plotting analysis as shown by FIG. 2. The partial peptide of the receptor protein having the amino acid sequence represented by SEQ ID NO: 2 is that containing the parts which have been analyzed to be extracellular domains (hydrophilic domains) in the hydrophobic plotting analysis as shown by FIG. 4. A peptide containing a hydrophobic domain part can be similarly used. In addition, the peptide may contain each domain separately or plural domains together.

Examples of the partial peptide include those having the amino acid sequences of the 78th to 130th amino acids, the 193rd to 204th amino acids, the 274th to the 307th amino acids, and the 387th to 398th amino acids of the amino acid sequence represented by SEQ ID NO: 1 as well as those having the amino acid sequences of the 139th to 191st amino acids, the 254th to 265th amino acids, the 335th to 368th and the 448th to 459th amino acids of the amino acid sequence represented by SEQ ID NO: 2.

Further, the partial peptide of the receptor protein of the present invention include variants of the above partial peptide, wherein the amino group of N-terminal methionine residue of the above receptor protein is protected with a protecting group (e.g., acyl group having 1 to 6 carbon atoms such as formyl group, acetyl group, etc.); the N-terminal region of the above receptor protein is cleaved in a living body and the glutamyl group formed is pyroglutaminated; or a substituent (e.g., —OH, —COOH, amino group, imidazole group, indole group, guanidino group, etc.) on the side chain of an amino acid in the molecule of the above receptor protein is protected with a suitable protecting group (e.g., acyl group having 1 to 6 carbon atoms such as formyl group, acetyl group, etc.), or conjugated peptides of the above partial peptide such as glycopeptides having sugar chains.

Normally, the C-terminal of the partial peptide of the present invention is a carboxyl group (—COOH) or carboxylate (—COO$^-$) and, like the receptor protein of the present invention, the C-terminal may be the amide or ester.

When the partial peptide of the present invention has a carboxyl group (or carboxylate) at a position other than the C-terminal, it may be amidated or esterified and such amide or ester is also included in the scope of the partial peptide of the present invention. The ester group may be the same group as that described with respect to the above C-terminal of the receptor protein.

As the salt of the partial peptide of the present invention, in particular, a physiologically acceptable acid addition salt is preferred. Examples of the salt include those with inorganic acids (e.g., hydrochloric acid, phosphoric acid, hydrobromic acid, sulfuric acid, etc.) and those with organic acids (e.g., acetic acid, formic acid, propionic acid, fumaric acid, maleic acid, succinic acid, tartaric acid, citric acid, malic acid, oxalic acid, benzoic acid, methanesulfonic acid, benznesulfonic acid, etc.).

The partial peptide or its salt of the present invention can be prepared according to a per se known peptide synthesis method or by cleaving the receptor protein of the present invention with a suitable peptidase.

As the peptide synthesis method, for example, either of solid phase synthesis and liquid phase synthesis can be employed. That is, the objective peptide can be produced by condensing a partial peptide or amino acid sequence which can contain the partial peptide of the present invention with the remaining part and deprotecting a protecting group, if any. Conventional condensing methods and deprotecting methods can be employed and they are described by, for example, M. Bodanszky and M. A. Ondetti, Peptide Synthesis, Interscience Publishers, New York (1966); Schroeder and Luebke, The Peptide, Academic Press, New York (1965); Nobuo Izumi et al., Fundamental and Experiment of Peptide Synthesis, Maruzen (1975); Haruaki Yazima and Syunpei Skakibara, Biochemistry Experiment Lecture, Protein Chemistry IV, 205 (1977); Haruaki Yazima, Second Series Drug Development Vol. 14, Peptide Synthesis, Hirokawa Shoten.

After completion of the reaction, the partial peptide of the present invention can be purified and isolated by combining conventional purification methods such as solvent extraction, distillation, column chromatography, liquid chromatography, recrystallization and the like. In case the partial peptide thus obtained is a free peptide, it can be converted into its appropriate salt according a known method. On the other hand, if the peptide obtained is in the form of a salt, it can be converted into the corresponding free peptide.

The DNA encoding the receptor protein of the present invention may be any DNA in so far as it contains the nucleotide sequence encoding the above-described receptor protein of the present invention. The DNA may be any of genomic DNA, genomic DNA library, cDNA derived from the above-described cells and tissues, cDNA library derived from the above-described cells and tissues and synthetic DNA. The vector to be used for the library may be any of bacteriophage, plasmid, cosmid, phagemid and the like. In addition, the DNA can be amplified by reverse transcriptase polymerase chain reaction (hereinafter abbreviated to RT-PCR) with a mRNA fraction prepared from the above-described cells and tissues.

Specifically, the DNA encoding the receptor protein having the same or substantially the same amino acid sequence represented by SEQ ID NO: 1 of the present invention may be, for example, DNA having the nucleotide sequence represented by SEQ ID NO: 3 or any DNA having a nucleotide sequence hybridizable to the nucleotide sequence represented by SEQ ID NO: 3 under high stringent conditions and encoding a receptor protein which has the same activities, i.e., ligand binding activity, signal information transmission activity and the like as those of the receptor protein peptide having the amino acid sequence represented by SEQ ID NO: 1. Examples of the hybridizable DNA include DNA having at least about 70% to about 80% homology, preferably, at least about 90% homology, more preferably, at least about 95% homology to the nucleotide sequence represented by SEQ ID NO: 3.

More specifically, as the DNA encoding the receptor protein containing the amino acid sequence represented by SEQ ID NO: 1, the DNA having the nucleotide sequence represented by SEQ ID NO: 3 or the like can be used.

The DNA encoding the receptor protein having the same or substantially the same amino acid sequence represented by SEQ ID NO: 2 of the present invention may be, for example, DNA having the nucleotide sequence represented by SEQ ID NO: 4 or any DNA having a nucleotide sequence hybridizable to the nucleotide sequence represented by SEQ ID NO: 4 under high stringent conditions and encoding a receptor protein which has the same activities, i.e., ligand binding activity, signal information transmission activity and the like as those of the receptor protein peptide having the amino acid sequence represented by SEQ ID NO: 2. Examples of the hybridizable DNA include DNA having at least about 70% to about 80% homology, preferably, at least about 90% homology, more preferably, at least about 95% homology to the nucleotide sequence represented by SEQ ID NO: 4.

More specifically, as the DNA encoding the receptor protein containing the amino acid sequence represented by SEQ ID NO: 2, the DNA having the nucleotide sequence represented by SEQ ID NO: 4 or the like can be used. The nucleotide sequence represented by SEQ ID NO: 4 is a variant of the nucleotide sequence of SEQ ID NO: 3 having an addition of 183 bases at its 5'-terminal.

Hybridization can be carried out by a per se known method or its modification, for example, under high stringent conditions.

The high stringent conditions used herein are, for example, those of sodium concentration at about 19 mM to about 40 mM, preferably about 19 mM to about 20 mM and a temperature at about 50° C. to about 70° C., preferably about 60° C. to about 65° C. In particular, hybridization conditions of sodium concentration at about 19 mM and a temperature at about 65° C. are most preferred.

The DNA encoding the partial peptide of the present invention may be any DNA in so far as it contains the nucleotide sequence encoding the above-described partial peptide of the present invention. The DNA may be any of genomic DNA, genomic DNA library, cDNA derived from the above-described cells and tissues, cDNA library derived from the above-described cells and tissues and synthetic DNA. The vector to be used for the library may be any of bacteriophage, plasmid, cosmid, phagemid and the like. In addition, the DNA can be amplified by reverse transcriptase polymerase chain reaction (hereinafter abbreviated to RT-PCR) with a mRNA fraction prepared from the above-described cells and tissues.

Specifically, the DNA encoding the partial peptide of the receptor protein having the same or substantially the same amino acid sequence represented by SEQ ID NO: 1 of the present invention may be, for example, DNA having the nucleotide sequence represented by SEQ ID NO: 3 or any DNA having a nucleotide sequence hybridizable to the nucleotide sequence represented by SEQ ID NO: 3 under high stringent conditions and encoding a receptor protein which has the same activities, i.e., ligand binding activity, signal information transmission activity and the like as those of the receptor protein peptide having the amino acid sequence represented by SEQ ID NO: 1. Examples of the hybridizable DNA include DNA having at least about 70% to about 80% homology, preferably, at least about 90% homology, more preferably, at least about 95% homology to the nucleotide sequence represented by SEQ ID NO: 3.

For example, as the DNA encoding the partial peptide of the receptor protein containing the amino acid sequence represented by SEQ ID NO: 1, the DNA having the nucleotide sequence represented by SEQ ID NO: 3 or the like can be used. More specifically, as the DNA encoding the partial peptide having the amino acid sequences of the 78th to 130th amino acids, the 193rd to 204th amino acids, the 274th to the 307th amino acids or the 387th to 398th amino acids of the amino acid sequence represented by SEQ ID NO: 1, the DNA having the nucleotide sequence of the 232nd to 390th bases, the 577th to 612th bases, the 820th to 921st bases or the 1159th to 1194th bases of the nucleotide sequence represented by SEQ ID NO: 3 can be used.

The DNA encoding the partial peptide of the receptor protein having the same or substantially the same amino acid sequence represented by SEQ ID NO: 2 of the present invention may be, for example, DNA having the nucleotide sequence represented by SEQ ID NO: 4 or any DNA having a nucleotide sequence hybridizable to the nucleotide sequence represented by SEQ ID NO: 4 under high stringent conditions and encoding a receptor protein which has the same activities, i.e., ligand binding activity, signal information transmission activity and the like as those of the receptor protein peptide having the amino acid sequence represented by SEQ ID NO: 2. Examples of the hybridizable DNA include DNA having at least about 70% to about 80% homology, preferably, at least about 90% homology, more preferably, at least about 95% homology to the nucleotide sequence represented by SEQ ID NO: 4.

For example, like the DNA encoding the partial peptide of the receptor protein containing the amino acid sequence represented by SEQ ID NO: 2, the DNA having the nucleotide sequence represented by SEQ ID NO: 4 or the like can be used. More specifically, like the DNA encoding the partial peptide having the amino acid sequences of the 139th to 191th amino acids, the 254th to 265th amino acids, the 335th to the 368th amino acids or the 448th to 459th amino acids of the amino acid sequence represented by SEQ ID NO: 2, the DNA having the nucleotide sequence of the 415th to 573rd bases, the 760th to 795th bases, the 1003rd to 1104th bases or the 1342nd to 1377th bases of the nucleotide sequence represented by SEQ ID NO: 4 can be used.

Deposited materials

A deposit containing a human G-protein coupled receptor protein DNA has been deposited with the National Institute of Bioscience and Human-Technology Agency of Industrial Science and Technology. Also as noted above, the deposit is referred to herein as "the deposited clone."

The deposited clone was deposited with the National Institute of Bioscience and Human-Technology Agency of Industrial Science and Technology, 1-3, Higashi 1 chome Tsukuba-shi Ibaraki-ken, 305 JAPAN, on Oct. 25, 1996, and assigned Deposit No. FERM BP-5724.

The deposited material is *E. coli* HB101/pHEBF2 that contains cDNA clones, including those of human G-protein coupled receptor protein DNA.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. section 112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Hybridization can be carried out by a per se known method or its modification, for example, under high stringent conditions.

As described above, the high stringent conditions used herein are, for example, those of sodium concentration at about 19 mM to about 40 mM, preferably about 19 mM to about 20 mM, and a temperature at about 50° C. to about 70° C., preferably about 60° C. to about 65° C. In particular, hybridization conditions of sodium concentration at about 19 mM and a temperature at about 65° C. are most preferred.

As the means for cloning the DNA encoding the entire receptor protein of the present invention, there is amplification by PCR using synthetic DNA primers containing partial nucleotide sequences of the receptor protein of the present invention. Alternatively, DNA integrated into a suitable vector is selected by hybridization with labeled DNA fragment or a synthetic DNA encoding a part or entire region of the receptor protein of the present invention. The hybridization is carried out, for example, according to the method described in Molecular Cloning 2nd Ed.; J. Samrook et al., Cold Spring Harber Lab. Press, (1989). A commercially available library can be used according to the direction of the attached manufacurer's protocol.

Conversion of the nucleotide sequence of DNA can be carried out according to a per se known method such as Gupped douplex method or Kunkel method or its modification by using a known kit, Mutan™-G of Mutan™-K (both Takara Shuzo Co., Ltd., ™ represents trademark). The nucleotide sequence represented by SEQ ID NO: 1 can be produced by deleting 183 bases from the 5'-terminal of the nucleotide sequence represented by SEQ ID NO: 2.

The cloned DNA encoding the receptor protein can be used as such according to a particular purpose. Alternatively, if desired, it can be used after digestion with one or more restriction enzymes or a linker can be added. The DNA may have the codon, ATG, as a translation initiation codon at its 5' terminal side and the codon, TAA, TGA or TAG as a translation termination codon at its 3' terminal side. These translation initiation and termination codons can be added by using a suitable synthetic DNA adapter.

The expression vector of the receptor protein of the present invention can be prepared, for example, by (a) cutting out the desired DNA fragment from the DNA encoding the receptor protein of the present invention and (b) joining the DNA fragment to a suitable expression vector at the downstream from a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches with a host to be used for gene expression. In the case of using animal cells as the host, examples of the promoter include SRα promoter, SV40 promoter, LTR promoter, CMV promoter, HSV-TK promoter, etc. Among them, CMV promoter or SRα promoter is preferred. In the case of using bacteria of the genus Escherichia as the host, preferred examples of the promoter include trp promoter, lac promoter, recA promoter, $\lambda P_L$ promoter, lpp promober, etc. In the case of using bacteria of the genus Bacillus as the host, preferably, SPO1 promoter, SPO2 promoter, penP promoter, etc. can be used. In the case of using yeast as the host, preferred examples of the promoter include PHO5 promoter, PGK promoter, GAP promoter, ADH promoter, etc. In the case of using insect cells as the host, preferred examples of the promoter include polyhedrin prompter, P10 promoter, etc.

In addition to the above, optionally, the expression vector may further contain enhancer, splicing signal, poly A addition signal, selection marker, SV40 replication origin (hereinafter sometimes abbreviated to SV40 ori) etc. Examples of the selection marker include dihydrofolate reductase (hereinafter sometimes abbreviated to dhfr) gene [methotrexate (MTX) resistance], ampicillin resistant gene (hereinafter sometimes abbreviated to Amp$^r$), neomycin resistant gene (hereinafter sometimes abbreviated to Neo, G418 resistance), etc. In particular, when CHO (dhfr$^-$) cell is used together with DHFR gene as the selection marker, selection can also be carried out by using a thymidine free medium.

If necessary, a signal sequence which matches with a host is added to the N-terminal side of the receptor protein of the present invention. As the signal sequence, there may be mentioned alkaline phosphatase signal sequence, OmpA signal sequence, etc. in the case of using bacteria of the genus Escherichia as the host; α-amylase signal sequence, subtilisin signal sequence, etc. in the case of using bacteria of the genus Bacillus as the host; mating factor α signal sequence, invertase signal sequence, etc. in the case of using yeast as the host; insulin signal sequence, α-interferon signal sequence, antibody molecule signal sequence, etc. in the case of using animal cells as the host, respectively.

The DNA encoding receptor protein of the present invention thus constructed can be employed to transform the host.

As the host, for example, there may be mentioned bacteria of the genus Escherichia, bacteria of the genus Bacillus, yeast, insect cells, insects and animal cells, etc.

Specific examples of bacteria of the genus Escherichia include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of bacteria of the genus Bacillus include *Bacillus subtilis* MI114 [Gene, 24, 255 (1983)], 207–21 [Journal of Biochemistry, 95, 87 (1984)], etc.

Examples of yeast include *Saccaromyces cereviseae* AH22, AH22$^-$, NA87-11A, DKD-5D, 20B-12, etc.

Examples of insect cells include *Spodoptera frugiperda* cell (Sf cell), MG1 cell derived from mid-intestine of *Trichoplusia ni,* High Five™ cell derived from egg of *Trichoplusia ni,* cells derived from *Mamestra brassicae,* cells derived from *Estigmena acrea,* etc. for the virus, AcNPV; and *Bombyx mori* N cell (BmN cell), etc. for the virus, BmNPV. As the Sf cell, for example, Sf9 cell (ATCC CRL1711) and Sf21 cell described by Vaughn, J. L., in Vitro, 13, 213–217 (1977) can be used.

As the insect, for example, a larva of *Bombyx mori* can be used [Maeda et al., Nature, 315, 592 (1985)].

Examples of animal cells include monkey cell COS-7, Vero, Chinese hamster cell CHO, DHFR gene deficient Chinese hamster cell CHO (dhfr$^-$ CHO cell), mouse L cell, mouse AtT-20, mouse myeloma cell, rat GH 3, human FL cell, etc.

Transformation of bacteria of the genus Escherichia is carried out, for example, according to the method described in Proc. Natl. Acad. Sci. U.S.A., 69, 2110 (1972) or Gene, 17, 107 (1982).

Transformation of bacteria of the genus Bacillus is carried out, for example, according to the method described in Molecular & General Genetics, 168, 111 (1979).

Transformation of yeast is carried out, for example, according to the method described in Proc. Natl. Acad. Sci. U.S.A., 75, 1929 (1978).

Transformation of insect cells or insect is carried out, for example, according to the method described in Bio/Technology, 6, 47–55(1988).

Transformation of animal cells is carried out, for example, according to the method described in Virology, 52, 456 (1973).

Thus, the transformant transformed with the expression vector containing the DNA encoding the G-protein coupled receptor protein can be obtained.

In the case of the bacterial host of the genus Escherichia or Bacillus, the transformant can be suitably cultivated in a liquid culture medium and materials required for growth of the transformant such as carbon sources, nitrogen sources, inorganic materials, etc. are added to the medium. Examples of the carbon sources include glucose, dextrin, soluble starch, sucrose, etc. The nitrogen sources include, for example, inorganic or organic materials such as ammonium salts, nitrate salts, corn steep liquor, peptone, casein, meat extract, soybean meal, potato extract, etc. The inorganic materials include, for example, calcium chloride, sodium dihydrogen phosphate, magnesium chloride, etc. In addition, yeast, vitamins, growth promoting factors etc. can be added. Preferably, the medium is adjusted to pH about 5 to about 8.

Preferably, the medium for cultivating the bacteria of the genus Escherichia is, for example, M9 medium containing glucose and Casamino Acids (Miller, Journal of Experiments in Molecular Genetics, 431–433, Cold Spring Harbor Laboratory, New York, 1972). If necessary, in order to activate the promoter efficiently, for example, an agent such as 3β-indolyl acrylic acid can be added to the medium.

In the case of the bacterial host of the genus Escherichia, normally, the transformant is cultivated at about 15° C. to about 43° C. for about 3 hours to about 24 hours. If necessary, the culture can be aerated or stirred.

In the case of the bacterial host of the genus Bacillus, normally, the transformant is cultivated at about 30° C. to about 40° C. for about 6 hours to about 24 hours. If necessary, the culture can be aerated or stirred.

In the case of the yeast host, the transformant is cultivated in, for example, Burkholder's minimal medium [Bostian, K. L. et al., Proc. Natl. Acad. Sci. U.S.A., 77, 4505 (1980) and SD medium containing 0.5% Casamino Acids [Bitter, G. A., Proc. Natl. Acad. Sci. U.S.A., 81, 5330 (1984)]. Preferably, the medium is adjusted to pH about 5 to about 8. Normally, the transformant is cultivated at about 20° C. to about 35° C.

for about 24 hours to about 72 hours. If necessary, the culture can be aerated or stirred.

In case of the insect cell host or insect host, the transformat is cultivated in, for example, Gace's Insect Medium [Grace, T. C. C.,. Nature, 195, 788 (1962)] to which an appropriate additive such as inactivated 10% bovine serum is added. Preferably, the medium is adjusted to pH about 6.2 to about 6.4. Normally, the transformant is cultivated at about 27° C. for about 3 days to about 5 days and, if necessary, the culture can be aerated or stirred.

In the case of the animal cell host, the transformant is cultivated in, for example, MEM medium containing about 5% to about 20% fetal bovine serum [Science, 122, 501 (1952)], DMEM medium [Virology, 8, 396 81959)], RPMI 1640 medium [The Journal of the American Medical Association, 199, 519 (1967)], 199 medium [Proceeding of the Society for the Biological Medicine, 73, 1 (1950)], etc. Preferably, the medium is adjusted to pH about 6 to about 8. Normally, the transformant is cultivated at about 30° C. to about 40° C. for about 15 hours to about 60 hours and, if necessary, the culture can be aerated or stirred.

As described hereinabove, the G-protein coupled receptor protein of the present invention can be produced at the cell membrane of the transformant.

Separation and purification of the receptor protein of the present invention from the above culture can be carried out, for example, as follows.

Extraction of the receptor protein of the present invention from the transformant culture can be carried out by an appropriate known method. For example, after cultivation, the transformant is recovered by a per se known method and suspended in a suitable buffer. Then, the transformant is disrupted by a per se known method such as ultrasonication, treatment with lysozyme and/or freeze-thaw cycling, followed by separating a crude extract of the receptor protein by centrifugation, filtration, etc. The buffer may contain a protein modifier such as urea, guanine hydrochloride or a surfactant such as Triton X-100™, etc. When the receptor protein is secreted in the culture broth, after completion of cultivation, its supernatant can be separated from the transformant cells to collect the supernatant.

Purification of the receptor protein contained in the culture supernatant thus obtained or the extract can be carried out by combining per se known separation and purification methods appropriately. As the per se known separation and purification methods, there may be mentioned a method utilizing difference in solubilities such as salting out, solvent precipitation, etc.; a method mainly utilizing difference in molecular weights such as dialysis, ultrafiltration, gel filtration, SDS-polyacrylamide gel electrophoresis, etc.; a method utilizing difference in electric charges such as ion exchange chromatography, etc.; a method utilizing difference in specific affinities such as affinity chromatography, etc.; a method utilizing difference in hydrophobic properties such as reverse phase high performance liquid chromatography, etc.; a method utilizing difference in isoelectric points such as isoelectric point electrophoresis: and the like.

When the free receptor protein is obtained, it can be converted into its salt by a per se known method or its modification. On the other hand, when the receptor protein is obtained in the form of a salt, it can be converted into the free receptor protein or a different salt by a per se known method or its modification.

The receptor protein produced by the recombinant can be treated with an appropriate protein modifying enzyme prior to or after purification to appropriately modify the protein or to partially remove a polypeptide. Examples of the protein modifying enzyme include trypsin, chymotrypsin, arginyl endopeptidase, protein kinase, glycosidase and the like.

The activity of thus-produced receptor protein or its salt of the present invention can be determined by a binding test with a labeled ligand or an enzyme immunoassay with a specific antibody.

The receptor protein, its partial peptide or their salts, and DNAs encoding them of the present invention can be employed (a) in a method for determination of a ligand to the receptor protein of the present invention, (b) for obtaining an antibody or an antiserum, (c) for construction of an expression system of the recombinant receptor protein, (d) for development of a receptor binding assay system and screening for candidate compounds for drugs using the expression system, (e) for practice of drug design based on comparison with structurally analogous ligands and receptors, (f) as reagents for preparation of probes to be used in gene diagnosis, PCR primers, etc., (g) as drugs for gene prophylaxis and therapy, and the like.

In particular, screening for agonists or antagonists to the G-protein coupled receptor protein which are specific to a human being and another mammal can be carried out by using a receptor binding assay system utilizing an expression system of the recombinant G-protein coupled receptor protein of the present invention, and the agonists and antagonists can be used as prophylactic and therapeutic drugs for various diseases.

More specific description of the use of the receptor protein, its partial peptide or their salts, DNAs encoding the receptor protein or its partial peptide and antibody will be set forth below.

(I) Determination method of a ligand to the G-protein receptor protein

The receptor protein of the present invention or its salt, or the partial protein or its salt of the present invention is useful as a reagent for investigation or determination of a ligand to the receptor protein or its salt of the present invention.

That is, the present invention provides a method for determination of a ligand to the receptor protein of the present invention comprising bringing the receptor protein or its partial peptide of the present invention or a salt thereof into contact with a test compound.

Examples of the test compound include tissue extract, cell culture supernatant of a human being or another mammal (e.g., mouse, rat, pig, cattle, sheep, monkey, etc.), or the like, in addition to the above-described known ligands, such as angiotensin, bombesin, cannabinoid, cholecystokinin, glutamine, serotonin, melatonin, neuropeptide Y, opioid, purine, vasopressin, oxytocin, PACAP, secretin, glucagon, calcitonin, adrenomedullin, somatostatin, GHRH, CRF, ACTH, GRP, PTH, VIP (vasoactive intestinal and related polypeptides), dopamine, motilin, amylin, bradykinin, CGRP (calcitonin gene related proteins), leukotriene, pancreastacin, prostaglandin, thromboxane, adenosine, adrenalin, α or β-chemokine (e.g., IL-8, GROα, GROβ, GROγ, NAP-2, ENA-78, PF4, IP10, GCP-2, MCP-1, HC14, MCP-3, I-309, MIP-1α, MIP-1β, RANTES, etc.), endothelin, enterogastrin, histamine, neurotensin, TRH, pancreatic polypeptides or gallamine. For example, the tissue extract or the cell culture supernatant is added to the receptor protein of the present invention and the mixture is fractionated by measuring a cell stimulation activity, etc. to finally obtain a single ligand.

Specifically, the ligand determination method of the present invention is carried out by using the receptor protein or its partial peptide of the present invention or a salt thereof, or by constructing an expression system of the recombinant receptor protein and using a receptor binding assay system utilizing the expression system to determine a compound (e.g., peptide, protein, non-peptide compound, synthetic compound, fermentation product, etc.) showing a cell stimulation activity (e.g., an activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phosphorylation of intracellular protein, activation of c-fos, lowering of pH, etc.) upon binding to the receptor protein of the present invention.

The ligand determination method of the present invention is characterized by measurement of, for example, an amount of a test compound bound to the receptor protein or the partial peptide or a cell stimulation activity upon bringing the receptor protein or the partial peptide into contact with the test compound.

More specifically, the ligand determination method of the present invention is:

(a) a method for determination of a ligand to the receptor protein or its salt of the present invention which comprises labeling a test compound, and measuring an amount of the labeled test compound bound to the receptor protein, the partial peptide or their salts upon bringing the receptor protein, the partial peptide or their salts into contact with the labeled test compound;

(b) a method for determination of a ligand to the receptor protein or its salt of the present invention which comprises labeling a test compound, and measuring an amount of the labeled test compound bound to cells containing the receptor protein or a membrane fraction of the cells upon bringing the labeled test compound into contact with the cell or the cell membrane fraction;

(c) a method for determination of a ligand to the receptor protein which comprises labeling a test compound, and measuring an amount of the labeled test compound bound to the G-protein coupled receptor protein expressed on the cell membrane of a transformant containing the DNA encoding the receptor protein of the present invention by cultivating the transformant upon bringing the labeled test compound into contact with the expressed G-protein coupled receptor protein;

(d) a method for determination of a ligand to the receptor protein or its salt of the present invention which comprises measuring a cell stimulation activity (e.g., an activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phosphorylation of intracellular protein, activation of c-fos, lowering of pH, etc.) mediated by the receptor protein upon bringing a test compound into contact with cells containing the receptor protein;

(e) a method for determination of a ligand to the receptor protein or which comprises which comprises which comprises measuring a cell stimulation activity (e.g., an activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phospholylation of intracellular protein, activation of c-fos, lowering of pH, etc.) mediated by the receptor protein upon bringing a test compound into contact with the receptor protein expressed on the cell membrane of a transformant containing DNA encoding the receptor protein of the present invention by cultivating the transformant.

The receptor protein used in the ligand determination of the present invention may be any protein in so far as it contains the above-described receptor protein or partial peptide of the present invention. In particular, the receptor protein expressed in a large amount by using animal cells is suitable.

For producing the receptor protein of the present invention, the above-described expression process can be used. In particular, it is preferred to carry out expression of the DNA encoding the receptor protein in cells of mammals or insects. Normally, cDNA is used as a DNA fragment encoding the desired part of the protein, but the present invention is not necessarily limited to this. For example, a gene fragment or a synthetic DNA can also be used. For transferring a DNA fragment encoding the receptor protein of the present invention into a host animal cell and expressing it efficiently, it is preferred to integrate the DNA fragment into the downstream from a polyhetrin promoter of nuclear polyhetosis virus (NPV) belonging to baculovirus whose host is insect, a promoter derived from SV40, retrovirus promoter, metallothionein promoter, human heat shock promoter, cytomegalovirus promoter, SRA promoter or the like. The quantitative and qualitative assay of expression of the receptor protein can be carried out by a per se known method. For example, the assay can be carried out according to the method described by Nambi, P. et al., J. Biol. Chem., 267, 19555–19559 (1992).

In the ligand determination of the present invention, the receptor protein, its partial peptide or their salts may be the receptor protein, its partial peptide or their salts as such which are purified according to a per se known method, or a material containing the receptor protein, its partial peptide or their salts such as cells containing the receptor protein or their membrane fractions.

In the case of using the cells containing the receptor protein of the present invention, they may be immobilized with glutaraldehyde, formalin, etc. Immobilization can be carried out by a per se known method.

The cells containing the receptor protein of the present invention are host cells expressing the receptor protein of the present invention. The Examples of the host cells include E. coli, Bacillus subtilis, yeast, insect cells, animal cells and the like.

The cell membrane fraction is a fraction containing many cell membranes obtained by disrupting cells and then treated by a per se known method. The disruption of cells can be carried out, for example, using Potter-Elvehjem homogenizer, Waring blender or Polytron (Kinematica), ultrasonication, French press, etc. Fractionation of the cell membrane fraction can mainly be carried out by fractionation centrifugation, density-gradient centrifugation or the like. For example, a disrupted cell suspension is centrifuged at a low rate (500 rpm–3000 rpm) for a short period of time (normally, about 1 minute–10 minutes) and further the supernatant is centrifuged at a high rate (15000 rpm–30000 rpm) for about 30 minutes to about 2 hours to obtain a cell membrane fraction as precipitate. This cell membrane fraction contains the expressed receptor protein and many membrane components such as phospholipids, membrane proteins and the like.

The amount of the receptor protein contained in the cells or the cell membrane fraction is preferably $10^3$ to $10^8$ molecules, more preferably $10^5$ to $10^7$ molecules per one cell. As the expression level is higher, a ligand binding activity (specific activity) becomes higher, which makes not only construction of a high sensitive screening system but also determination of a large number of samples in one lot possible.

For carrying out the above ligand determination methods (a) to (c), a suitable receptor protein fraction and a labeled test compound are required.

The receptor protein fraction is preferably a naturally occurring receptor protein fraction or a recombinant receptor protein fraction having the equivalent activity to that of the naturally occurring receptor protein. The equivalent activity used herein means the equivalent ligand binding activity, signal information transmission activity or the like.

The labeled test compound is preferably the above-exemplified ligand such as angiotensin, bombesin, cannabinoid, cholecystokinin, glutamine, serotonin, melatonin, neuropeptide Y, opioid, purine, vasopressin, oxytocin, PACAP, secretin, glucagon, calcitonin, adrenomedullin, somatostatin, GHRH, CRF, ACTH, GRP, PTH, VIP (vasoactive intestinal and related polypeptides), dopamine, motilin, amylin, bradykinin, CGRP (calcitonin gene related proteins), leukotriene, pancreastacin, prostaglandin, thromboxane, adenosine, adrenalin, α or β-chemokine (e.g., IL-8, GROα, GROβ, GROγ, NAP-2, ENA-78, PF4, IP10, GCP-2, MCP-1, HC14, MCP-3, I-309, MIP-1α, MIP-1β, RANTES, etc.), endothelin, enterogastrin, histamine, neurotensin, TRH, pancreatic polypeptides or gallamine labeled with [$^3$H], [$^{125}$I], [$^{14}$C], [$^{35}$S], etc.

Specifically, for carrying out the ligand determination method of the present invention, the cells or cell membrane fraction containing the receptor protein of the present invention are suspended in a buffer suitable for the determination method to prepare a receptor standard. Any buffer which does not interfere with the binding between the ligand and the receptor protein can be used, for example, a phosphate buffer of pH 4 to 10, preferably pH 6 to 8, Tris-HCl buffer or the like. In order to minimize non-specific binding, a surfactant such as CHAPS, Tween-80™ (Kao-Atlas), digitonin, deoxycholate, etc. and various proteins such as bovine serum albumin, gelatin, etc. to the buffer. In addition, for inhibiting degradation of the receptor protein and ligand by a protease, a protease inhibitor such as PMSF, leupeptin, E-64 (Peptide Kenkyu-sho), pepstatin, etc. can also be added to the buffer. A given amount (5000 cpm–500000 cpm) of the test compound labeled with [$^3$H], [$^{125}$I], [$^{14}$C], [$^{35}$S] or the like is added to 0.01 ml to 10 ml of the receptor suspension. For evaluating an amount of non-specific binding (NSB), a reaction tube, to which a large excess amount of the unlabeled test compound is added, is provided. The reaction is carried out at about 0° C. to about 50° C., preferably about 4° C. to about 37° C. for about 20 minutes to about 24 hours, preferably about 30 minutes to about 3 hours. After completion of the reaction, the reaction mixture was filtered through, for example, glass fiber filter paper, washed with a suitable amount of the same buffer and the radioactivity remaining in the glass fiber filter paper is counted with a liquid scintillation counter or a γ-counter. The test compound whose count (B-NSB) obtained by subtracting the amount of non-specific binding (NSB) from the total binding amount (B) exceeds 0 cpm can be selected as the ligand to the receptor protein or its salt of the present invention.

The above ligand determination methods (d) and (e) can be carried out by measuring a cell stimulation activity (e.g., activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phospholylation of intracellular protein, activation of c-fos, lowering of pH, etc.) mediated by the receptor protein of the present invention by a known method or a commercially available determination kit. Specifically, first, the cells containing the receptor protein are cultivated in a well plate, etc. For ligand determination, the culture medium is replaced with a fresh medium or a suitable buffer which does not have cytotoxicity. After addition of a test compound, the culture is incubated for a given period of time, followed by extracting the cells or recovering the supernatant to determine a product formed by a method suitable for determination of the product. Where an assay of the formation of an index compound of a cell stimulating activity (e.g., arachidonic acid, etc.) is difficult due to a degradation enzyme contained in the cells, the assay can be carried out with addition of an inhibitor of the degradation enzyme. In addition, as for cAMP production inhibitory activity or the like, the activity can be detected as the production inhibitory activity of cells whose basic production is increased with forskolin, etc.

The determination kit of a ligand which binds to the receptor protein or its salt of the present invention comprises as an essential component the receptor protein or the partial peptide of the present invention, cells containing the receptor protein of the present invention or a salt thereof, a cell membrane fraction of cells containing the receptor protein of the present invention, or the like.

Examples of the kit for ligand determination of the present invention include as follows.

(1) Reagent for ligand determination (a) Measurement buffer and washing buffer

A buffer obtained by addition of 0.05% of bovine serum albumin (Sigma) to Hanks' balanced salt solution (Gibco). The buffer is sterilized by filtration through a filter of 0.45 μm in pore diameter and then stored at 4° C. or it can be prepared when it is used.

(b) Standard of G-protein coupled receptor protein

CHO cells expressing the receptor protein of the present invention are subjected to passage in an amount of $5 \times 10^5$ cells/well in a 12-well plate and cultivated at 37° C. for 2 days in 5% $CO_2$-95% air to obtain a standard of the receptor protein.

(c) Labeled test compound

A test compound labeled with a commercial available [$^3$H], [$^{125}$I], [$^{14}$C], [$^{35}$S], etc. or another suitable label.

An aqueous solution of the labeled test compound is stored at 4° C. or −20° C. and, when it is used, it is diluted to 1 μM with the measurement buffer. As for a water-insoluble or slightly water-soluble compound, the compound is dissolved in dimethylformamide, DMSO, methanol, etc.

(d) Non-labeled test compound

The same test compound as that of the labeled test compound is used to prepare a solution in 100 to 1000 times concentration.

(2) Measurement (a) The receptor protein expressing CHO cells cultivated in a 12-well tissue culture plate is washed twice with 1 ml of the measurement buffer and then 490 μl of the buffer is added to the respective wells.

(b) 5 μl of the labeled test compound is added and reacted at room temperature for one hour.

(c) The reaction mixture is removed and the wells are washed three times with 1 ml of the washing buffer. The labeled test compound bound to the cells is dissolved with 0.2 N NaOH-1% SDS and mixed with 4 ml of liquid scintillator A (Wako Pure Chemical Industries, Ltd.).

(d) Radioactivity is measured by a liquid scintillation counter (Beckman).

The ligand which can bind to the receptor protein of the present invention is, for example, that specifically present in brain, pituitary, pancreas, etc. Specific examples thereof include the above-exemplified ligands, that is, angiotensin, bombesin, cannabinoid, cholecystokinin, glutamine, serotonin, melatonin, neuropeptide Y, opioid, purine, vasopressin, oxytocin, PACAP, secretin, glucagon, calcitonin, adrenomedullin, somatostatin, GHRH, CRF, ACTH, GRP, PTH, VIP (vasoactive intestinal and related polypeptides), dopamine, motilin, amylin, bradykinin, CGRP (calcitonin gene related proteins), leukotriene, pancreastacin, prostaglandin, thromboxane, adenosine, adrenalin, $\alpha$ or $\beta$-chemokine (e.g., IL-8, GRO$\alpha$, GRO$\beta$, GRO$\gamma$, NAP-2, ENA-78, PF4, IP10, GCP-2, MCP-1, HC14, MCP-3, I-309, MIP-1$\alpha$, MIP-1$\beta$, RANTES, etc.), endothelin, enterogastrin, histamine, neurotensin, TRH, pancreatic polypeptides or gallamine.

(II) Gene prophylactic and therapeutic drug of the G-protein coupled receptor protein deficiency diseases If a ligand to the receptor protein of the present invention is found out by the above method (I), DNA encoding the receptor protein of the present invention can be used as a drug for gene prophylaxis and therapy of diseases caused by deficiency of the G-protein coupled receptor protein deficiency depending upon a particular activity of the ligand.

For example, when there is a patient whose physiological activity of a ligand is scarcely expected because of decrease in the receptor protein of the present invention, the amount of the receptor protein in the patient's body can be increased to exhibit the sufficient activity of the ligand, for example, by (i) administering DNA encoding the receptor protein of the present invention to the patient to express it, or (ii) inserting DNA encoding the receptor protein of the present invention into subject cells to express it, followed by transplantation of the cells into the patient. Then, DNA encoding the receptor protein of the present invention is useful as a safe and low toxic drug for gene prophylaxis and therapy of disease caused by deficiency of the receptor protein of the present invention.

DNA encoding the receptor protein of the present invention (hereinafter sometimes abbreviated to the DNA of the present invention) alone or, after inserted into a suitable vector such as retroviral vector, adenoviral vector, adenovirus associated viral vector, etc., can be used as the above prophylactic and therapeutic drug according to a conventional method. For example, the DNA of the present invention can be used in the form of tablets, if necessary, providing sugar coating, capsules, elixirs, microcapsules, etc. for oral administration, or in the form of injectable preparations such as aseptic solutions or suspensions in water or other pharmaceutically acceptable solutions for parenteral administration. A pharmaceutical composition in a unit dosage form can be prepared by mixing the DNA of the present invention with, for example, one or more pharmaceutically acceptable carriers, flavors, excipients, vehicles, preservatives, stabilizers, binders, etc. according to generally acceptable manner. The effective component is contained in the composition in such an amount that a dose in the intended desired range can be obtained.

Examples of additives to be mixed in tablets, capsules, etc. include binders such as gelatin, corn starch, tragacanth gum and gum arabic, excipients such as crystalline cellulose, swelling agents such as corn starch, gelatin and alginic acid, lubricants such as magnesium stearate, sweetenings such as sucrose, lactose and saccharin, flavors such as peppermint, akamono oil and cherry, and the like. In the case of the capsule dosage unit form, in addition to the above component, it can contain a liquid carrier such as fat or oil. An injectable aseptic composition can be prepared according to a conventional manner, for example, by dissolving or suspending the active component in a vehicle such as injectable water and a natural vegetable oil such as sesame oil, coconut oil, etc. Examples of the injectable aqueous solution include physiological saline, isotonic solutions containing glucose and other adjuvants (e.g., D-sorbitol, D-mannitol, sodium chloride, etc.) and suitable dissolution aids, for example, alcohols (e.g., ethanol), polyalcohols (e.g., propylene glycol, polyethylene glycol), nonionic surfactants (e.g., Polysorbate 80™, HCO-50) may be further added. As an oily solution, for example, sesame oil, soybean oil, etc. can be used and a dissolution aid such as benzyl benzoate or benzyl alcohol, etc. can be further added.

The above prophylactic and therapeutic drugs can further contain, for example, buffers (e.g., phosphate buffer, sodium acetate buffer), smoothing agents (e.g., benzalkonium chloride, procaine hydrochloride, etc.), stabilizers (e.g., human serum albumin, polyethylene glycol, etc.), preservatives (e.g., benzyl alcohol, phenol, etc.), antioxidants, and the like. The injectable preparation thus produced is normally filled in a suitable ampoule. Since the pharmaceutical composition thus obtained is safe and low toxic, it can be administered to a human being and another mammal (e.g., rat, rabbit, sheep, pig, cattle, cat, dog, monkey, etc.). Although the amount of the DNA of the present invention to be administered is varied according to particular subjects, organs to be treated, symptoms, routes of administration, etc., in general, for oral administration to an adult human being (as 60 kg body weight), the DNA is administered in an amount of about 0.1 mg/day to about 100 mg/day, preferably about 1.0 mg/day to about 50 mg/day, more preferably about 1.0 mg to about 20 mg. For parenteral administration to an adult human being (as 60 kg body weight), it is advantageous to administer the composition in the form of an injectable preparation in an amount of about 0.01 mg/day to about 30 mg/day, preferably about 0.1 mg/day to about 20 mg/day, more preferably about 0.1 mg/day to about 10 mg/day, though the single dosage is varied according to particular subjects, organs to be treated, symptoms, routes of administration, etc. As for other animals, the composition can be administered in the above amount with converting it into that for the body weight of 60 kg.

(III) Gene diagnosing agent

The DNA encoding the receptor protein or the partial peptide of the present invention can be used for detecting an abnormality of DNA encoding the receptor protein or the partial peptide of the present invention (abnormal gene) in a human being or another mammal (e.g., rat, rabbit, sheep, pig, cattle, cat, dog, monkey, etc.). Therefore, the DNA encoding the receptor protein or the partial peptide of the present invention is useful as a gene diagnosing agent for detecting abnormality of the DNA.

(IV) Determination method of ligand to the G-protein coupled receptor protein

The receptor protein, the partial peptide and their salts of the present invention have ligand binding properties and they can be used for determination of ligand concentration in the living body in a high sensitivity.

The method for determination of the present invention can be used, for example, in combination with a competitive method. That is, the ligand concentration can be determined by bringing a specimen into contact with the receptor protein, the partial peptide or a salt thereof of the present invention. Specifically, the determination method can be carried out, for example, according to the methods described in Hiroshi Irie, Ed., "Radioimmunoassay", Kodan-sha, 1974 and "Second Series Radioimmunoassay", Kodan-sha, 1979 or their modifications.

(V) Method for screening for compounds which alter binding of a ligand to the G-protein coupled receptor protein Compounds which alter binding of a ligand to the receptor protein or its salt (e.g., peptides, proteins, non-peptide compounds, synthetic compounds, fermentation products) can be screened efficiently by using the receptor protein, the partial peptide or their salts of the present invention, or by constructing an expression system of the recombinant receptor protein and using a receptor binding assay system utilizing the expression system. Examples of these compounds include compounds having cell stimulation activities (e.g., activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phosphorylation of intracellular protein, activation of c-fos, lowering of pH, etc.) mediated by the receptor protein of the present invention (i.e., so-called agonists to the receptor protein of the present invention) and compounds which do not have such activities (i.e., so-called antagonists to the receptor protein of the present invention).

That is, the present invention provides a method for screening for compounds which alter binding of a ligand to the receptor protein or its salt of the present invention, or their salts which comprises comparing (i) binding of the ligand to the receptor protein or the partial peptide of the present invention or a salt thereof upon bringing the receptor protein or the partial peptide of the present invention or a salt thereof into contact with the ligand, and (ii) that upon bringing the receptor protein or the partial peptide of the present invention or a salt thereof into contact with the ligand and a test compound.

In the screening method of the present invention, an amount of the ligand bound to the receptor protein, the partial peptide or a salt thereof, a cell stimulation activity or the like is measured and compared upon bringing the receptor protein or the partial peptide of the present invention or a salt thereof into contact with the ligand, and (ii) that upon bringing the receptor protein or the partial peptide of the present invention or a salt thereof into contact with the ligand and a test compound.

More specifically, the screening method of the present invention includes:

(a) a method for screening for compounds which alter binding of a ligand to the receptor protein or its salt of the present invention, or their salts which comprises labeling the ligand, and measuring and comparing (i) an amount of the labeled ligand bound to the receptor protein or the partial peptide of the present invention or a salt thereof upon bringing the receptor protein or the partial peptide of the present invention or a salt thereof into contact with the labeled ligand, and (ii) that upon bringing the receptor protein or the partial peptide of the present invention or a salt thereof into contact with the labeled ligand and a test compound;

(b) a method for screening for compounds which alter binding of a ligand to the receptor protein or its salt of the present invention, or their salts which comprises labeling the ligand, and measuring and comparing (i) an amount of the labeled ligand bound to cells containing the receptor protein or a membrane fraction of the cells upon bringing the labeled ligand into contact with the cells or the membrane fraction, and (ii) that upon bringing the labeled ligand and a test compound into contact with the cells or the membrane fraction;

(c) a method for screening for compounds which alter binding of a ligand to the receptor protein or its salt of the present invention, or their salts which comprises labeling the ligand, and measuring and comparing (i) an amount of the labeled ligand bound to the receptor protein expressed on the cell membrane of a transformant containing DNA encoding the receptor protein of the present invention by cultivating the transformant upon bringing the labeled ligand into contact with the expressed receptor protein, and (ii) that upon bringing the labeled ligand and a test compound into contact with the expressed receptor protein;

(d) a method for screening for compounds which alter binding of a ligand to the receptor protein or its salt of the present invention, or their salts which comprises measuring and comparing (i) a cell stimulation activity (e.g., activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phospholylation of intracellular protein, activation of c-fos, lowering of pH, etc.) mediated by the receptor upon bringing a compound which activates the receptor protein of the present invention (e.g., a ligand to the receptor protein of the present invention) into contact with cells containing the receptor protein of the present invention, and (ii) that upon bringing the compound which activates the receptor protein and a test compound into contact with the cells;

(e) a method for screening for compounds which alter binding of a ligand to the receptor protein or its salt of the present invention, or their salts which comprises measuring and comparing (i) a cell stimulation activity (e.g., activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phosphorylation of intracellular protein, activation of c-fos, lowering of pH, etc.) mediated by the receptor upon bringing a compound which activates the receptor protein of the present invention (e.g., a ligand to the receptor of the present invention) into contact with the receptor protein expressed on the cell membrane of a transformant containing DNA encoding the receptor protein by cultivating the transformant, and (ii) that upon bringing the compound which activates the receptor protein of the present invention and a test compound into contact with the receptor protein expressed on the cell membrane;

Before the receptor protein of the present invention is available, for screening for a G-protein coupled receptor agonist or antagonist, first, it is necessary to obtain candidate compounds by using cells, tissues or a cell membrane fraction thereof containing the G-protein coupled receptor protein of rat, etc (primary screening) and then to confirm whether or not the candidate compounds actually inhibit the binding of human G-protein coupled receptor protein and a ligand (secondary screening). When cells tissues or a cell membrane thereof are used as such, other receptor proteins are present, which make screening for an agonist or antagonist to the objective receptor protein difficult. However, for example, if the human receptor protein of the present invention is used, the primary screening is not required and efficient screening for compounds which inhibit the binding of a ligand to the G-protein coupled receptor protein can be carried out. In addition, whether the compound thus screened for is an agonist or an antagonist can be readily evaluated.

The receptor protein used in the screening method of the present invention may be any protein in so far as it contains the above-described receptor protein or partial peptide of the present invention. A cell membrane fraction of a mammalian internal organ containing the receptor protein of the present invention is suitable. However, in particular, the internal organs of a human being are hardly available and therefore the receptor protein expressed in a large amount by using a recombinant is suitable for the screening.

For producing the receptor protein of the present invention, the above-described expression process can be used. In particular, it is preferred to carry out expression of the DNA encoding the receptor protein in cells of mammals or insects. Normally, cDNA is used as a DNA fragment encoding the desired part of the protein, but the present invention is not necessarily limited to this. For example, a gene fragment or a synthetic DNA can also be used. For transferring a DNA fragment encoding the receptor protein of the present invention into a host animal cell and expressing it efficiently, it is preferred to integrate the DNA fragment into the downstream from a polyhetrin promoter of nuclear polyhetosis virus (NPV) belonging to baculovirus whose host is insect, a promoter derived from SV40, retrovirus promoter, metallothionein promoter, human heat shock promoter, cytomegalovirus promoter, SRα promoter or the like. The quantitative and qualitative assay of the expressed receptor can be carried out by a per se known method. For example, the assay can be carried out according to the method described by Nambi, P. et al., J. Biol. Chem., 267, 19555–19559 (1992).

In the screening method of the present invention, the receptor protein, its partial peptide or their salts may be the receptor protein, its partial peptide or the salt as such which is purified according to a per se known method, or a material containing the receptor protein, its partial peptide or their salts such as cells containing the receptor protein or their membrane fractions.

In the case of using the cells containing the receptor protein of the present invention, they may be immobilized with glutaraldehyde, formalin, etc. Immobilization can be carried out by a per se known method.

The cells containing the receptor protein of the present invention are host cells expressing the receptor protein of the present invention. Preferred examples of the host cells include *E. coli, Bacillus subtilis,* yeast, insect cells, animal cells and the like.

The cell membrane fraction is a fraction containing many cell membranes obtained by disrupting cells and then treated by a per se known method. The disruption of cells can be carried out, for example, using Potter-Elvehjem homogenizer, Waring blender or Polytron (manufactured by Kinematica), ultrasonication, French press, etc. Fractionation of the cell membrane fraction can mainly be carried out by fractionation centrifugation, density-gradient centrifugation or the like. For example, a disrupted cell suspension is centrifuged at a low rate (500 rpm–3000 rpm) for a short period of time (normally, about 1–10 minutes) and further the supernatant is centrifuged at a high rate (15000 rpm–30000 rpm) for about 30 minutes to about 2 hours to obtain a cell membrane fraction as a precipitate. This cell membrane fraction contains the expressed receptor protein and many membrane components such as phospholipids, membrane proteins and the like.

The amount of the receptor protein contained in the cells containing the receptor protein or the cell membrane fraction is preferably $10^3$ to $10^8$ molecules, more preferably $10^5$ to $10^7$ molecules per one cell. As the expression level is higher, a ligand binding activity (specific activity) becomes higher, which makes not only construction of a high sensitive screening system but also determination of a large number of samples in one lot possible.

For carrying out the above screening methods (a) to (c), a suitable receptor protein fraction and a labeled test compound are required. The receptor protein fraction is preferably a naturally occurring receptor protein fraction or a recombinant receptor protein fraction having the equivalent activity to that of the naturally occurring receptor protein. The equivalent activity used herein means equivalent ligand binding activity, signal information transmission activity or the like.

The labeled ligand includes labeled ligands and labeled ligand analog compounds. For example, the ligand labeled with [$^3$H], [$^{125}$I], [$^{14}$C], [$^{35}$S], etc. can be used.

Specifically, for carrying out the screening method of the present invention, the cells or cell membrane fraction containing the receptor protein of the present invention are suspended in a buffer suitable for the screening to prepare a receptor protein standard. Any buffer which does not interfere with the binding between the ligand and the receptor protein can be used, for example, a phosphate buffer of pH 4 to 10, preferably pH 6 to 8, Tris-HCl buffer or the like. In order to minimize non-specific binding, a surfactant such as CHAPS, Tween-80™ (Kao-Atlas), digitonin, deoxycholate, etc. and various proteins such as bovine serum albumin, gelatin, etc. to the buffer. In addition, for inhibiting degradation of the receptor protein and the ligand by a protease, a protease inhibitor such as PMSF, leupeptin, E-64 (manufactured by Peptide Kenkyu-sho), pepstatin, etc. can also be added to the buffer. A given amount of the labeled ligand (5000 cpm–500000 cpm) is added to 0.01 ml to 10 ml of the receptor suspension and, at the same time, $10^{-4}$ M to $10^{-10}$ M of a test compound is present in the receptor suspension. For evaluating an amount of non-specific binding (NSB), a reaction tube to which a large excess amount of the unlabeled ligand is added is provided. The reaction is carried out about 0° C. to about 50° C., preferably about 4° C. to about 37° C. for about 20 minutes to about 24 hours, preferably about 30 minutes to about 3 hours. After completion of the reaction, the reaction mixture was filtered through, for example, a glass fiber filter paper, washed with a suitable amount of the same buffer and the radioactivity remaining in the glass fiber filter paper is counted with a liquid scintillation counter or a γ-counter. The test compound whose specific binding count (B-NSB) is 50% or lower can be selected as a candidate compound capable of inhibiting antagonism, when taking the count ($B_0$-NSB) obtained by subtracting the count of non-specific binding (NSB) from the count ($B_0$) obtained without any antagonistic material as 100%.

The above screening methods (d) and (e) can be carried out by measuring a cell stimulation activity (e.g., activity to enhance or inhibit release of arachidonic acid, release of acetyl choline, release of intracellular $Ca^{2+}$, formation of intracellular cAMP, formation of intracellular cGMP, production of inositol phosphate, change of cell membrane potential, phosphorylation of intracellular protein, activation of c-fos, lowering of pH, etc.) mediated by the receptor protein of the present invention by a known method or a commercially available determination kit. Specifically, first, the cells containing the receptor protein are cultivated in a multi-well plate, etc. For carrying out screening, the culture medium is replaced with a fresh medium or a suitable buffer which does not have cytotoxicity. After addition of a test compound, the culture is incubated for a given period of time, followed by extracting the cells or recovering the supernatant to determine a product formed by a method suitable for determination of the product. Where an assay of the formation of an index compound of a cell stimulating activity (e.g., arachidonic acid, etc.) is difficult due to a degradation enzyme contained in the cells, the assay can be carried out with addition of an inhibitor of the degradation enzyme. In addition, as for cAMP production inhibitory activity or the like, the activity can be detected as the production inhibitory activity of cells whose basic production has been increased with forskolin, etc.

For carrying out the screening by measurement of a cell stimulating activity, cells expressing a suitable receptor protein are required. As cells expressing the receptor protein of the present invention, for example, naturally occurring cell strains containing the receptor protein of the present invention or the above-described recombinants expressing the receptor protein are preferred.

Examples of the test compounds include peptides, proteins, non-peptide compounds, synthetic compounds, cell extracts, vegetable extracts, animal tissue extracts and the like and these compounds may be novel compounds or known compounds.

The kit for screening for a compound which alters binding of a ligand to the receptor protein or its salt of the present invention comprises as an essential component the receptor protein or the partial peptide of the present invention or a salt thereof, cells containing the receptor protein of the present invention, a cell membrane fraction of cells containing the receptor protein of the present invention, or the like.

Examples of the screening kit of the present invention include as follows.

(1) Reagent for screening (a) Measurement buffer and washing buffer

A buffer obtained by addition of 0.05% of bovine serum albumin (Sigma) to Hanks' balanced salt solution (Gibco). The buffer is sterilized by filtration through a filter of 0.45 $\mu$m in pore diameter and then stored at 4° C. or it can be prepared when it is used.

(b) Standard of G-protein coupled receptor protein

CHO cells expressing the receptor protein of the present invention are subjected to passage in an amount of $5 \times 10^5$ cells/well in a 12-well plate and cultivated at 37° C. for 2 days in 5% $CO_2$-95% air to obtain a standard of the receptor protein.

(c) Labeled ligand

A ligand labeled with a commercial available [$^3$H], [$^{125}$I], [$^{14}$C], [$^{35}$S], etc. or another suitable label.

An aqueous solution of the labeled test compound is stored at 4° C. or –20° C. and, when it is used, it is diluted to 1 $\mu$M with the measurement buffer.

(d) Ligand standard solution

A ligand is dissolved in PBS containing 0.1% bovine serum albumin (Sigma) at the final concentration of 1 mM and stored at –20° C.

(2) Measurement (a) The receptor protein expressing CHO cells cultivated in a 12-well tissue culture plate is washed twice with 1 ml of the measurement buffer and then 490 $\mu$l of the same buffer is added to the respective wells.

(b) 5 $\mu$l of a $10^{-3}$ to $10^{-10}$ M solution of a test compound is added and then 5 $\mu$l of the labeled ligand is added. They are reacted at room temperature for one hour. In order to evaluate a non-specific binding amount, 5 $\mu$l $10^{-3}$ M ligand is added.

(c) The reaction mixture is removed and the wells are washed three times with 1 ml of the washing buffer. The labeled ligand bound to the cells is dissolved with 0.2 N NaOH-1% SDS and mixed with 4 ml of liquid scintillator A (Wako Pure Chemical Industries, Ltd.).

(d) Radioactivity is measured by a liquid scintillation counter (Beckman). Percent Maximum Binding (PMB) is calculated by the equation [1]:

$$PMB=[(B-NSB)/(B_0-NSB)] \times 100$$

wherein PMB is Percent Maximum Binding, B is a value obtained with addition of a specimen, NSB is a value of non-specific binding, and $B_0$ is a maximum binding value.

The compound or its salt obtained by using the screening method of the screening kit of the present invention alters binding of a ligand to the receptor protein or its salt of the present invention. Specifically, it is a compound or a salt thereof which binds to the receptor protein of the present invention and exhibits cell stimulating activity mediated by the receptor protein (i.e., so-called an agonist to the receptor protein of the present invention) or which binds to the receptor protein of the present invention but does not exhibit the cell stimulating activity (i.e., so-called an antagonist of the present invention).

Examples of the compounds include peptides, proteins, non-peptide compounds, synthetic compounds, fermented products and the like and they may be novel compounds or known compounds.

Since the agonist to the receptor protein of the present invention has the same physiological activity as that of a ligand to the receptor protein, it is useful as an active component of a safe and low toxic pharmaceutical composition having the ligand activity.

On the other hand, since the antagonist to the receptor protein of the present invention can inhibit the physiological activity of a ligand to the receptor protein, it is useful as an active component of a safe and low toxic pharmaceutical composition for inhibiting the ligand activity.

If the compound or its salt obtained by the screening method or the screening kit of the present invention is used for a pharmaceutical composition as described above, any conventional manner can be employed. For example, the compound or its salt of the present invention can be used in the form of tablets, if necessary, providing sugar coating, capsules, elixirs, microcapsules, etc. for oral administration, or in the form of injectable preparations such as aseptic solutions or suspensions in water or other pharmaceutically acceptable solutions for parenteral administration. A pharmaceutical composition in a unit dosage form can be prepared by mixing the compound or its salt of the present invention with, for example, one or more pharmaceutically acceptable carriers, flavors, excipients, vehicles, preservatives, stabilizers, binders, etc. according to generally acceptable manner. The effective component is contained in the composition in such an amount that a dose in the intended desired range can be obtained.

Examples of additives to be mixed in tablets, capsules, etc. include binders such as gelatin, corn starch, tragacanth gum and gum arabic, excipients such as crystalline cellulose, swelling agents such as corn starch, gelatin and alginic acid, lubricants such as magnesium stearate, sweetenings such as sucrose, lactose and saccharin, flavors such as peppermint, akamono oil and cherry, and the like. In case of a capsule dosage unit form, in addition to the above components, it can contain a liquid carrier such as fat or oil. An injectable aseptic composition can be prepared according to a conventional manner, for example, by dissolving or suspending the active component in a vehicle such as injectable water and a natural vegetable oil such as sesame oil, coconut oil, etc. Examples of injectable aqueous solution include physiological saline, isotonic solutions containing glucose and other adjuvants (e.g., D-sorbitol, D-mannitol, sodium chloride, etc.) and suitable dissolution aids, for example, alcohols (e.g., ethanol), polyalcohols (e.g., propylene glycol, polyethylene glycol), nonionic surfactants (e.g., Polysorbate 80™, HCO-50) may be further added. As an oily solution, for example, sesame oil, soybean oil, etc. can be used and a dissolution aid such as benzyl benzoate or benzyl alcohol, etc. can be further added. The composition can further contain, for example, buffers (e.g., phosphate buffer, sodium acetate buffer), smoothing agents (e.g., benzalkonium chloride, procaine hydrochloride, etc.), stabilizers (e.g., human serum albumin, polyethylene glycol, etc.), preservatives (e.g., benzyl alcohol, phenol, etc.), antioxidants, and the like. The injectable preparation thus produced is normally filled in an appropriate ampoule.

Since the pharmaceutical composition thus obtained is safe and low toxic, it can be administered to a human being and another mammal (e.g., rat, rabbit, sheep, pig, cattle, cat, dog, monkey, etc.).

Although the amount of the compound or its salt of the present invention to be administered is varied according to particular subjects, internal organs to be treated, symptoms, routes of administration, etc. in general, for oral administration to an adult human being (as 60 kg body weight), the DNA is administered in an amount of about 0.1 mg/day to about 100 mg/day, preferably about 1.0 mg/day to about 50 mg/day, more preferably about 1.0 mg to about 20 mg. For parenteral administration to an adult human being (as 60 kg body weight), it is advantageous to administer the composition in the form of an injectable preparation in an amount of about 0.01 mg/day to about 30 mg/day, preferably about 0.1 mg/day to about 20 mg/day, more preferably about 0.1 mg/day to about 10 mg/day, though the single dosage is varied according to particular subjects, internal organs to be treated, symptoms, routes of administration, etc. As for other animals, the composition can be administered in the above amount with converting it into that for the body weight of 60 kg.

(VI) Preparation of antibody or antiserum against the G-protein coupled receptor protein, the partial peptide or salts thereof An antibody (e.g., monoclonal antibody, polyclonal antibody) or antiserum against the receptor protein, the partial peptide or their salts of the present invention can be prepared by using the receptor protein or the partial peptide of the present invention or a salt thereof as the antigen according to a conventional antibody or antiserum preparation process. For example, a monoclonal antibody can be prepared as follows.

Preparation of monoclonal antibody (a) Preparation of monoclonal antibody producer cells The receptor protein or the partial peptide of the present invention or a salt thereof (hereinafter sometimes abbreviated to the receptor protein, etc.) as such or together with a suitable carrier or diluent is administered to a site of a mammal which permits the antibody production. For enhancing the antibody production capability, complete Freund's adjuvant or incomplete Freund's adjuvant may be administered. Normally, the receptor, etc. is administered once every 3 weeks to 6 weeks, in total, about 2 to about 10 times. The mammals to be used include monkey, rabbit, dog, guinea pig, mouse, rat, sheep, goat, chicken and the like and mouse or rat is preferred.

For preparing monoclonal antibody producer cells, an individual whose antibody titer has been confirmed is selected from warm blood animals immunized with the antigen, for example, rat and, 2 days to 5 days after the final immunization, its spleen or lymph node is collected and antibody producer cells contained therein are fused with myeloma cells to prepare the desired monoclonal antibody producer hybridoma. Measurement of the antibody titer in an antiserum can be carried out, for example, by reacting the labeled receptor protein, etc. as described hereinafter and an antiserum and then measuring the activity of the labeling agent bound to the antibody. The cell fusion can be carried out according to a known method, for example, the method described by Koehler and Milstein, Nature, 256, 495 (1975). As a fusion promoter, for example, polyethylene glycol (PEG) or Sendai virus (HVJ), preferably PEG can be used.

Examples of myeloma cells include NS-1, P3U1, SP2/0, AP-1 and the like and P3U1 is preferred. The proportion of the number of antibody producer cells (spleen cells) and the number of myeloma cells to be used is preferably about 1:1 to about 20:1 and PEG (preferably PEG 1000–PEG 6000) is added in concentration of about 10% to about 80%. Cell fusion can be carried out efficiently by incubating a mixture of both cells at about 20° C. to about 40° C., preferably about 30° C. to about 37° C. for about 1 minute to about 10 minutes.

Various methods can be used for screening for a hybridoma producing the antibody against the receptor protein, etc. For example, there may be mentioned a method wherein a supernatant of the hybridoma is added to a solid phase (e.g., microplate) to which the receptor protein antibody is adsorbed directly or together with a carrier and then an anti-immunoglobulin antibody (if cells of a mouse are used in cell fusion, anti-mouse immunoglobulin antibody is used) of Protein A labeled with a radioactive substance or an enzyme is added to detect the monoclonal antibody against the receptor protein, etc. bound to the solid phase, and a method wherein a supernatant of the hybridoma is added to a solid phase to which an anti-immunoglobulin antibody or Protein A is adsorbed and then the receptor protein, etc., labeled with a radioactive substance or an enzyme is added to detect the monoclonal antibody against the receptor protein, etc. bound to the solid phase.

Selection of the monoclonal antibody can be carried out according to a per se known method or its modification. Normally, a medium for animal cells to which HAT (hypoxanthine, aminopterin, thymidine) are added is employed. Any selection and growth medium can be employed in so far as the hybridoma can grow. For example, RPMI 1640 medium containing 1% to 20%, preferably 10% to 20% fetal bovine serum, GIT medium containing 1% to 10% fetal bovine serum (Wako Pure Chemical Industries, Ltd.), a serum free medium for cultivation of a hybridoma (SFM-101, Nissui Seiyaku) and the like can be used. Normally, the cultivation is carried out at 20° C. to 40° C., preferably 37° C. for about 5 days to about 3 weeks, preferably 1 week to 2 weeks under about 5% $CO_2$ gas. The antibody titer of the supernatant of a hybridoma culture can be measured according to the same manner as described above with respect to the antibody titer of the anti-G-protein coupled receptor in the antiserum.

(b) Purification of monoclonal antibody

Separation and purification of a monoclonal antibody against the receptor protein, etc. (hereinafter sometimes referred to as the anti-receptor protein monoclonal antibody) can be carried out according the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

The antibody against the receptor protein, etc. of the present invention prepared by the above (a) and (b) can specifically recognize the receptor protein, etc. of the present invention and therefore it can be used in a quantitative determination of the receptor protein, etc. of the present invention in a specimen, particularly, a quantitative determination by a sandwich immunoassay. That is, the present invention also provides:

(a) a method for determination of the receptor protein or its salt of the present invention in a specimen fluid which comprises reacting an antibody against the receptor protein or the partial peptide of the present invention, the specimen fluid and the labeled receptor protein or the labeled partial peptide competitively and measuring the proportion of the labeled receptor protein or the labeled partial peptide bound to the antibody; and (b) a method for determination of the receptor protein or its salt of the present invention in a specimen fluid which comprises reacting the specimen fluid, an antibody insolubilized on a carrier and a labeled antibody simultaneously or continuously, and then measuring the activity of the labeling agent on the insolubilized carrier, one antibody being that recognizing the N-terminal of the receptor protein of the present invention and the other antibody being that reacting with the C-terminal of the receptor protein of the present invention.

In addition to the determination of the receptor protein or its salt of the present invention, the anti-receptor protein monoclonal antibody recognizing the receptor protein of the present invention, etc. can be used for detection by histological stains and the like. For these purposes, the antibody molecular as such can be used or F(ab')$_2$, Fab' or Fab fraction of the antibody molecule can also be used. A method for determination using an antibody against the receptor protein, etc. of the present invention is not specifically limited and any determination method can be used in so far as an amount of an antigen, antibody or antibody-antigen corresponding to an amount of an antigen in a fluid to be determined can be detected by a chemical or physical means and calculated based on a calibration curve prepared by using standard solutions containing known amounts of the antigen. For example, nephelometry, competitive method, immunometirc method and sandwich method are suitably employed. In particular, in view of sensitivity, specificity and the like, a sandwich method as described hereinafter is preferred.

As a labeling agent used in a determination method using a labeled reagent, radioisotopes, enzymes, fluorescent materials, luminous materials and the like can be used. Examples of radioisotopes include [$^{125}$I], [$^{131}$I], [$^3$H], [$^{14}$C] and the like. As the above enzymes, that having good stability and high specific activities is preferred and, for example, there are β-galactosidase, β-glucosidase, alkaline phosphatase, peroxidase, malate dehydrogenase and the like. As the fluorescent materials, for example, there are fluorescamine, fluorescein isothiocyanate and the like. As the luminous materials, there are luminol, luminol derivatives, luciferin, lucigenin and the like. In addition, biotin-avidin system can be used for binding of an antibody or antigen to a labeling agent.

For insolubilization of an antigen or antibody, physical adsorption can be used or, normally, a method using a chemical bond for insolubilizing or immobilizing a protein or an enzyme can be used. Examples of the carrier include insoluble polysaccharides such as agarose, dextran, cellulose and the like, synthetic resins such as polystyrene, polyacrylamide, silicone and the like, glass and the like.

In a sandwich method, a specimen fluid to be tested is reacted with an insolublized anti-receptor protein antibody (primary reaction) and further reacting a labeled anti-receptor protein antibody (secondary reaction), followed by measuring the labeling agent on the insoluble carrier to determine the amount of the receptor protein of the present invention in the specimen. The order of the primary and secondary reactions can be reversed and they can be carried out simultaneously or separately at different times. The above-described labeling agent and insolubilization can be applied to this method. In addition, in an immunoassay by a sandwich method, an antibody to be used as the solid phase antibody or labeled antibody is not necessary one kind of antibodies and, in order to improve measuring sensitivity, etc., a mixture of two or more kinds of antibodies can be used.

In the method for determination of the receptor protein, etc. by the sandwich method of the present invention, preferably, the antibodies against the receptor protein, etc. used in the primary and secondary reactions are those having different binding sites for the receptor protein. For example, when the antibody used in the secondary reaction is that recognizing the C-terminal region of the receptor protein, the antibodies used in the primary reaction are that recognizing an region other than the C-terminal region, for example, the N-terminal region.

The antibody against the receptor protein, etc. of the present invention can also be used for a measuring system other than a sandwich method, for example, a competitive method, immunometric method, nephelometry and the like. In a competitive method, an antigen in a specimen fluid and a labeled antigen are reacted with the antibody competitively and, after separation of the unreacted labeled antigen (F) from the labeled antigen bound to the antibody (B), measuring the amount of the labeling agent of either B or F to determine the amount of the antigen in the specimen fluid. In this reaction, both liquid phase method and solid phase method can be employed. In the liquid phase method, a soluble antibody is used as the antibody and B/F separation can be carried out by using polyethylene glycol, a second antibody against the above antibody. In the solid phase method, an immobilized solid phase antibody is used as the first antibody, or a soluble antibody is used as the first antibody and an immobilized solid phase antibody is used as the second antibody.

In the immunometric method, an antigen in a specimen fluid to be tested and an immobilized solid phase antigen are reacted with a given amount of a labeled antibody, competitively and then the solid phase is separated from the liquid phase. Alternatively, an antigen in a specimen fluid to be tested is reacted with an excess amount of a labeled antibody and an immobilized solid phase antigen is added to permit the unreacted labeled antibody to bind to the solid phase, followed by the separation of the solid phase from the liquid phase. Then, the amount of the labeling agent of either phase is measured to determine the amount of the antigen in the specimen fluid.

In nephelometry, an antigen-antibody reaction is carried out in a gel or solution and the amount of an insoluble precipitate formed is measured. Even when the amount of an antigen in a specimen fluid to be tested is small and the amount of a precipitate formed is small, laser nephelometry wherein diffusion of laser is utilized can be suitably employed.

When employing these immunoassay methods in the determination method of the present invention, to set any special conditions, procedures and the like is not required. That is, the determination system of the receptor protein or its salt of the present invention can be constructed based on conventional conditions and procedures in respective methods together with conventional artisan's technical consideration. As for details of these general technical means, reference can be made to various reviews, texts and the like, for example, Hiroshi Irie, Ed., Radioimmunoassay, Kodan-sha (1974); Hiroshi Irie, Ed, Second Series, Radioimmunoassay, Kodan-sha (1979); Eizi Ishikawa et al., Ed., Enzyme Immunoassay, Igaku-shoin (1978); Eizi Ishikawa et al., Ed., Second Series, Enzyme Immunoassay, Igaku-shoin (1982); Eizi Ishikawa et al., Third Series, Enzyme Immunoassay, Igaku-shoin (1987); Method in Enzymology, Vol. 70, Immunochemical Techniques (Part A)), Academic Press; ibid., Vol. 73, Immunochemical Techniques (Part B); ibid., Vol. 74, Immunochemical Techniques (Part C); ibid., Vol. 84, Immunochemical Techniques (Part D: Selected Immunoassays); ibid., Vol. 92, Immunochemical Techniques (Part E: Monoclonal Antibodies and General Immunoassay Methods); ibid., Vol. 121, Immunochemical Techniques (Part I: Hybridoma Technology and Monoclonal Antibodies and the like.

As described hereinabove, the receptor protein or its salt of the present invention can be determined at high sensitivity by using an antibody against the receptor protein, etc. of the present invention.

In the specification and drawings, the abbreviations of bases, amino acids and the like are those according to IUPAC-IUB Commission on Biochemical Nomenclature or those conventionally used in the art. The examples are as follows. When the amino acid has an optical isomer, the amino acid is L-isomer unless otherwise stated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecylsulfate EIA: enzyme immunoassay
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Me: methyl group
Et: ethyl group
Bu: butyl group
Ph: phenyl group
TC: thiazolidin-4(R)-carboxamide group The sequences in the Sequence Listing of the present specification are as follows.

SEQ ID NO: 1

This represents an amino acid sequence of the G-protein coupled receptor protein derived from a human brain.

SEQ ID NO: 2

This represents an amino acid sequence of the G-protein coupled receptor protein derived from a human brain, which is a variant of SEQ ID NO: 1 having additional 61 amino acids at the N-terminal thereof.

SEQ ID NO: 3

This represents a nucleotide sequence of DNA encoding the G-protein coupled receptor protein derived from a human brain having the amino acid sequence represented by SEQ ID NO: 1.

SEQ ID NO: 4

This represents a nucleotide sequence of DNA encoding the G-protein coupled receptor protein derived from a human brain having the amino acid sequence represented by SEQ ID NO: 2, which is a variant of SEQ ID NO: 3 having additional 183 bases at the 5'-terminal thereof.

SEQ ID NO: 5

A nucleotide sequence of EST which has been registered with a data base (NCBI abEST) under the accession number of T08099.

SEQ ID NO: 6

A nucleotide sequence of EST which has been registered with a data base (NCBI abEST) under the accession umber of T27053.

SEQ ID NO: 7

This represents a nucleotide sequence of a synthetic DNA used in screening for cDNA encoding the G-protein coupled receptor protein of the present invention.

SEQ ID NO: 8

This represents a nucleotide sequence of a synthetic DNA used in screening for cDNA encoding the G-protein coupled receptor protein of the present invention.

SEQ ID NO: 9

This represents a nucleotide sequence of a synthetic DNA used in screening for cDNA encoding the G-protein coupled receptor protein of the present invention.

SEQ ID NO: 10

This represents a nucleotide sequence of a synthetic DNA used in screening for cDNA encoding the G-protein coupled receptor protein of the present invention.

SEQ ID NO: 11

This represents a nucleotide sequence of a synthetic DNA used in screening for cDNA encoding the G-protein coupled receptor protein of the present invention.

SEQ ID NO: 12

This represents a nucleotide sequence of a synthetic DNA used in screening for cDNA encoding the G-protein coupled receptor protein of the present invention.

SEQ ID NO: 13

This represents a nucleotide sequence of a synthetic DNA used in screening for cDNA encoding the G-protein coupled receptor protein of the present invention.

SEQ ID NO: 14

This represents a nucleotide sequence of a synthetic DNA used in screening for cDNA encoding the G-protein coupled receptor protein of the present invention.

SEQ ID NO: 15

This represents a nucleotide sequence of a synthetic DNA used in screening for cDNA encoding the G-protein coupled receptor protein of the present invention.

The transformant *Escherichia coli* HB101/pHEBF2 obtained in Example 1 hereinafter has been deposited with National Institute of Bioscience and Human-Technology (NIBH), Agency of Industrial Science & Technology Ministry of International Trade & Industry (1-3, Higasi 1-chome, Tsukuba-shi Ibaraki, 305 Japan) according to the Budapest Treaty under the accession number of FERM BP-5724 since Oct. 25, 1996 and also deposited with Institute for Fermentation Osaka (IFO, 17-85, Juso-honmachi 2-chome Yodogawa-ku, Osaka, 532 Japan) under accession number of IFO 16044 since Oct. 21, 1996.

The following examples further illustrate the present invention in detail but are not to be construed to limit the scope thereof.

EXAMPLE 1

Obtaining cDNA of entire translated region of receptor protein from human poly(A)$^+$RNA and sequence analysis of its nucleotide sequence (1) Obtaining cDNA of translated region about C-terminal of the receptor protein from human fetal brain poly(A)$^+$R8NA by 3' RACE (Rapid Amplification of cDNA End) method and sequence analysis of its nucleotide sequence In order to obtain cDNA of the translated region about the C-terminal of the receptor protein encoded by the known nucleotide sequences, accession numbers of T08099 (SEQ ID NO: 5) and T27053 (SEQ ID NO: 6), 3'RACE method was carried out by using human fetal brain poly(A)$^+$RNA as a PCR template.

First, the following two primers were synthesized based on the known nucleotide sequences.

B1: (SEQ ID NO: 7)
5'-AAGTTGGCTGTCATCTGGGTGGGCTC-3'
B2: (SEQ ID NO: 8)
5'-TGAGCTCCTGCTGTGGCAGCTGGCACAG-3'

Then, a PCR template of 3'RACE method was prepared from 1 μg human fatal poly(A)$^+$RNA (Clontech) by using 3'RACE kit (Gibco BRL). The first PCR was carried out using the primer attached to 3'RACE kit and B1 primer. The conditions were 30 seconds at 95° C., 60 seconds at 65° C. and 180 seconds at 72° C., for 35 cycles and Ex Taq (Takara Shuzo) was used as the DNA polymerase. The second PCR reaction was carried out by using 1 μl of the first PCR mixture as the template under the same conditions for 35 cycles except that B2 primer was used instead of B1 primer. After electrophoresis, a band formed of 1.5 kb was recovered, subcloned by using a TA cloning kit (Invitrogen) and transferred into *E. coli* JM109. As a result of sequence analysis, it was found that the amplified band had the C-terminal region of the above-described known nucleotide sequences.

(2) Obtaining cDNA of translated region about N-terminal of the receptor protein from human fetal brain poly(A)$^+$RNA by 5'RACE method (marathon method) and sequence analysis of its nucleotide sequence In order to obtain cDNA of the translated region about the N-terminal of the receptor protein encoded by the above-described known nucleotide sequences, 5'RACE method was carried out by using human fetal brain poly(A)$^+$RNA as a PCR template.

First, the following two primers were synthesized based on the above-described known nucleotide sequences.

B8: (SEQ ID NO: 9)
5'-CATGCGGGCGTTCTGGTAGGTCATCAC-3'
B9: (SEQ ID NO: 10)
5'-GAAGAGGATGGGCAGGCAGAAGTAGCAG-3'

Then, a PCR template of 5'RACE method was prepared from 1 μg human fatal poly(A)$^+$RNA (Clontech) according to the manual of 5'RACE kit (Clontech). The first PCR was carried out using the primer attached to 5'RACE kit and B9 primer. The conditions were 10 seconds at 98° C. and 180 seconds at 72° C., for 5 cycles; 10 seconds at 98° C. and 180 seconds at 70° C., for 5 cycles; and 10 seconds at 98° C. and 180 seconds at 68° C., for 35 cycles. Ex Taq (Takara Shuzo) was used as the DNA polymerase. The second PCR reaction was carried out by using 1 μl of 50-fold dilution of the first PCR mixture as the template under the same conditions except that B8 primer was used instead of B9 primer. After electrophoresis, a band formed of about 1 kb was recovered and subcloned by using a TA cloning kit (Invitrogen), and sequence analysis was carried out according to the same manner as in the above (1). The presence of the 7-transmembrane receptor protein comprising 481 amino acids (SEQ ID NO: 1) encoded by the nucleotide sequence of from the 625th base (ATG; Met) to the 2067th base (TGC; Cys) as shown by FIG. 1 has been confirmed based on the results of the above (1) and (2). FIG. 2 shows the result of hydrophobic plotting of this amino acid sequence.

(3) The N-terminal side of the above receptor protein was further examined and 5'RACE method at the 5'side was further carried out to determine a transcription initiation codon.

The following two primers were synthesized based on the translation region of the receptor protein obtained in the above (2).

B11: (SEQ ID NO: 11)
5'-ATGAAGGGCACGGCACGACAAGAAACG-3'
B12: (SEQ ID NO: 12)
5'-ATGACAATAGGGAGGCAGAAAAAGAGG-3'

According to the same manner as in the above (2), a PCR template was prepared by using the above human fetal brain poly(A)$^+$RNA (Clontech) or human cerebellum poly(A)$^+$RNA (Nippon gene). Then, according to the same manner as described in the above (2), twice PCR were carried out by using the primer B11 instead of the primer B9 and the primer B12 instead of the primer B8, respectively to amplify the templates derived from the poly(A)+RNAs of the above internal organs. After electrophoresis of the reaction product, a band formed was recovered, subcloned by TA cloning and then subjected to sequence analysis.

As a result, the sequence obtained by combining the above (1) to (3) had the nucleotide sequence (SEQ ID NO: 4) of from the 442nd base (ATC; Met) to the 2067th base (TCG; Cys) as shown in FIG. 3 and was confirmed that it encoded the 7-transmembrane receptor protein comprising 542 amino acids (SEQ ID: NO 2). The result of the hydrophobic plotting of this sequence is shown in FIG. 4

The following primers were synthesized based on this sequence.

HEF: (SEQ ID NO: 13)
5'-GTCGACGAGATGTGTGAGGGCAGCAAAGAGTGC-3'

HER-1: (SEQ ID NO: 14)
5'-TACTGGGGCCTCAGCAAGGTGTGCCCAG-3'

PCR was carried out by using these two primers to amplify the coding region for the receptor protein from human fetal brain cDNA library. After subcloning in *E. coli*, a clone without any PCR error was selected and transformed into *E. coli* HB101 to obtain the transformant, *E. coli* HB101/pHEBF2. The DNA contained in the plasmid pHEBF2 has the nucleotide sequence represented by SEQ ID NO: 4 (FIG. 3) and the nucleotide sequence represented by SEQ ID NO: 3 is contained therein.

When PCR was carried out by using the above two primers under the conditions of 30 seconds at 95° C. and 90 seconds at 68° C. to amplify the coding region, the cDNA of the receptor protein as shown by FIG. 3 was obtained from fetal brain.

In order to obtain the cDNA of the receptor protein form adult brain, HEF-2 primer was synthesized instead of HEF primer.

HEF-2: (SEQ ID NO: 15)
5'-GTCGACTGGCTGTCTCCTGCTCATCCAGCCAT-3'

When adult brain poly(A)+RNA was amplified by using the primers HEF-2 and HEF-1, the cDNA encoding the receptor protein shown in FIG. 1 was obtained. The N-terminal of this receptor protein was shorter than that of the receptor protein shown in FIG. 3 by 61 amino acids.

The receptor protein shown in FIG. 1 has a consensus sequence called a Cossack sequence which indicates initiation of translation just before the translation initiation codon and a defined signal sequence in the N-terminal region. In view of these results, it has been found that the receptor protein shown by FIG. 1 is predominantly expressed in adult brain. On the other hand, cDNA encoding the receptor protein shown by FIG. 3 is obtained from fetal brain and the presence of the long chain receptor protein shown by FIG. 3 has also been confirmed.

EXAMPLE 2

Confirmation of expression specificity in various tissues

Northern blot was carried out by using cDNA encoding the receptor protein of the present invention contained in the plasmid pHEBF2 obtained in Example 1 as a probe.

Figure 5:
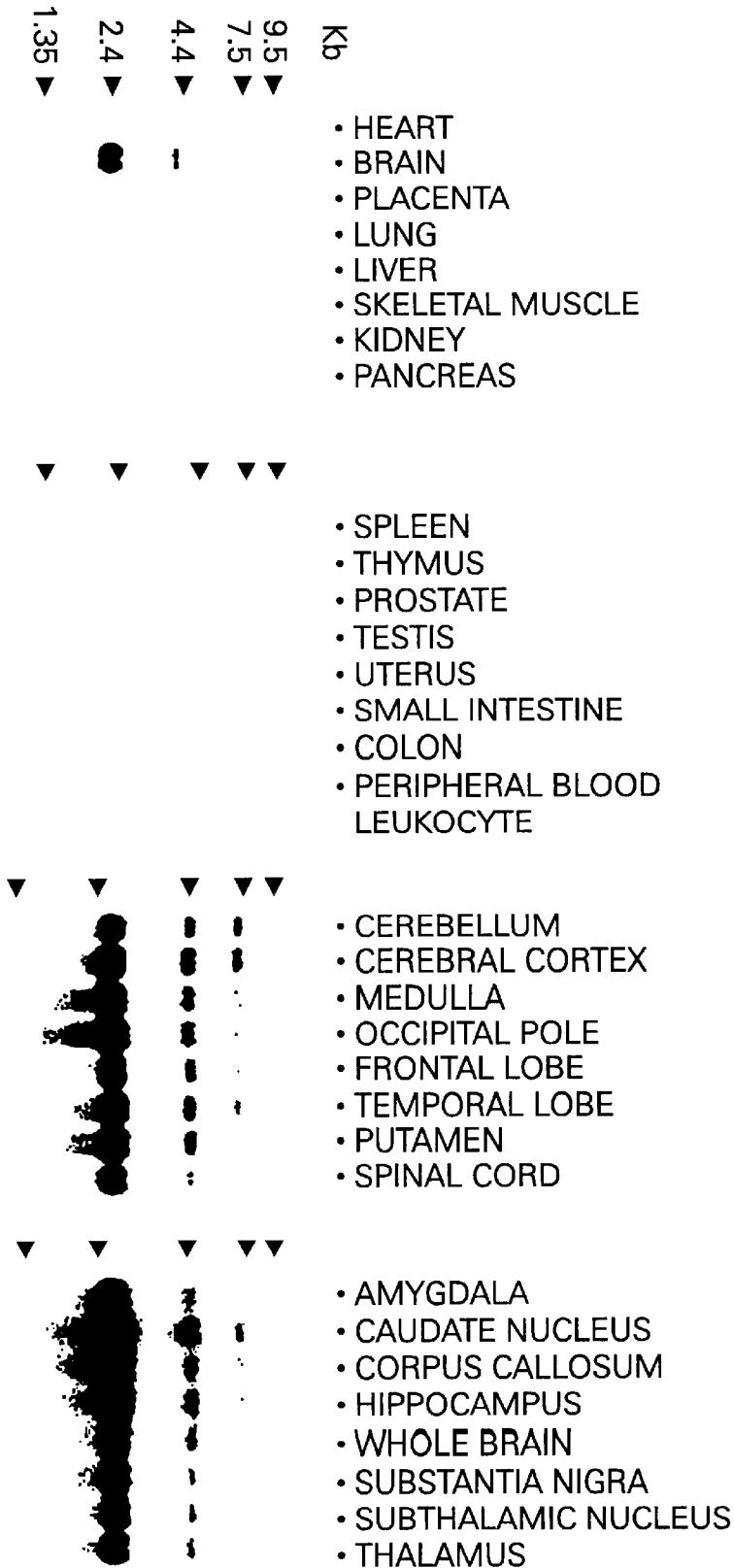
FIG. 5 illustrates the results of northan hybridization for examining expression levels of mRNA encoding the human G-protein coupled receptor protein of the present invention in various human tissues. The value (kb) represents the size of the RNA molecular weight marker.

The cDNA was labeled with Amarsham's multiprime kit and [$^{32}$P]dCTP according to the manual of the kit. Hybridization was carried out by using human MTN Blot (Clontech) and according to the manual attached thereto. Exposure of the filter to light was made as −80° C. for one week. As shown in FIG. 5, it has been found that this receptor protein mRNA is specifically expressed in brain.

As described hereinabove, the G-protein coupled receptor protein, its partial peptide or their salts and DNAs encoding them of the present invention can be used (a) for determination of ligands, (b) for obtaining antibodies and antisera, (c) for construction of recombinant receptor protein expression systems, (d) for development of receptor binding assay systems and screening for drug candidate compounds by using the expression systems, (e) for practice of drug design based on comparison of structurally analogous ligand receptors, (f) as reagents for preparing probes in gene diagnoses, PCR primers, etc., (g) drugs for gene prophylactic and therapy, and the like.

What is claimed is:

1. An isolated polynucleotide comprising a nucleotide sequence encoding the polypeptide comprising the amino acid sequence set forth in SEQ ID NO:1.

2. The isolated polynucleotide of claim 1 wherein said polynucleotide comprises the entire length of the nucleotide sequence set forth in SEQ ID NO:3.

3. An expression vector comprising the polynucleotide of claim 1.

4. An isolated host cell transfected with the vector of claim 3.

5. The isolated host cell of claim 4 wherein said host cell is *Escherichia coli* HB101/pHEBF2.

6. A process for preparing a polypeptide comprising the amino acid sequence set forth in SEQ ID NO:1, said process comprising cultivating the isolated host cell of claim 4 to produce said polypeptide and recovering said polypeptide from the culture.

7. The isolated polynucleotide of claim 1 comprising an RNA sequence corresponding to the entire length of the nucleotide sequence set forth in SEQ ID NO:3.

8. The isolated polynucleotide of claim 1 comprising an RNA sequence corresponding to the entire coding region of the nucleotide sequence set forth in SEQ ID NO:3.

9. An isolated polynucleotide which is fully complementary to the entire coding region of the nucleotide sequence set forth in SEQ ID NO:3.

10. The isolated polynucleotide of claim 9 which is fully complementary to the entire length of the nucleotide sequence set forth in SEQ ID NO:3.

11. An isolated polynucleotide comprising a nucleotide sequence encoding at least one amino acid sequence selected from the group consisting of amino acids 78 to 130 of SEQ ID NO:1, amino acids 193 to 204 of SEQ ID NO:1, amino acids 274 to 307 of SEQ ID NO:1, and amino acids 387 to 398 of SEQ ID NO:1.

12. An isolated polynucleotide comprising at least one nucleotide sequence selected from the group consisting of nucleotides 232 to 390 of SEQ ID NO:3, nucleotides 577 to 612 of SEQ ID NO:3, nucleotides 820 to 921 of SEQ ID NO:3, and nucleotides 1159 to 1194 of SEQ ID NO:3.

13. An isolated polynucleotide comprising the entire length of the nucleotide sequence set forth in SEQ ID NO:4.

14. An isolated polynucleotide comprising a nucleotide sequence encoding the amino acid sequence set forth in SEQ ID NO:2.

\* \* \* \* \*